United States Patent
Beckhove et al.

(10) Patent No.: US 9,994,854 B2
(45) Date of Patent: Jun. 12, 2018

(54) CYTOTOXIC T CELL RESPONSE MODIFIERS

(71) Applicant: Deutsches Krebsforschungszentrum, Heidelberg (DE)

(72) Inventors: Philipp Beckhove, Heidelberg (DE); Michael Boutros, Heidelberg (DE); Nisit Khandelwal, Heidelberg (DE); Marco Breinig, Bad Rappenau (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 0 days. days.

(21) Appl. No.: 14/914,585

(22) PCT Filed: Aug. 27, 2014

(86) PCT No.: PCT/EP2014/068183
§ 371 (c)(1),
(2) Date: Feb. 25, 2016

(87) PCT Pub. No.: WO2015/028515
PCT Pub. Date: Mar. 5, 2015

(65) Prior Publication Data
US 2016/0201066 A1 Jul. 14, 2016

Related U.S. Application Data

(60) Provisional application No. 61/870,421, filed on Aug. 27, 2013.

(51) Int. Cl.
| | |
|---|---|
| G01N 33/68 | (2006.01) |
| C12N 15/113 | (2010.01) |
| G01N 33/50 | (2006.01) |
| A61K 31/00 | (2006.01) |

(52) U.S. Cl.
CPC ......... *C12N 15/1138* (2013.01); *A61K 31/00* (2013.01); *G01N 33/5011* (2013.01); *G01N 33/5023* (2013.01); *G01N 33/6893* (2013.01); *C12N 2310/14* (2013.01); *G01N 2333/705* (2013.01)

(58) Field of Classification Search
None
See application file for complete search history.

(56) References Cited

U.S. PATENT DOCUMENTS

| | | |
|---|---|---|
| 2012/0244131 A1 | 9/2012 | Delacote et al. |
| 2012/0283324 A1 | 11/2012 | Appendino et al. |

FOREIGN PATENT DOCUMENTS

| | | |
|---|---|---|
| DE | 102006008074 A1 | 8/2007 |
| WO | WO-2008022104 A1 | 2/2008 |
| WO | 2011/050955 A1 | 5/2011 |

OTHER PUBLICATIONS

Bachmann et al., Distinct kinetics of cytokine production and cytolysis in effector and memory T cells after viral infection. Eur J Immunol. Jan. 1999;29(1):291-9.
Bellucci et al., Tyrosine kinase pathways modulate tumor susceptibility to natural killer cells. J Clin Invest. Jul. 2012;122(7):2369-83.
Berrien-Elliott et al., Durable adoptive immunotherapy for leukemia produced by manipulation of multiple regulatory pathways of CD8+ T-cell tolerance. Cancer Res. Jan. 15, 2013;73(2):605-16.
Blank et al., PD-L1/B7H-1 inhibits the effector phase of tumor rejection by T cell receptor (TCR) transgenic CD8+ T cells. Cancer Res. Feb. 1, 2004;64(3):1140-5.
Boutros et al., Analysis of cell-based RNAi screens. Genome Biol. 2006;7(7):R66.
Brackertz et al., FLT3-regulated antigens as targets for leukemia-reactive; cytotoxic T lymphocytes. Blood Cancer J. Mar. 2011;1(3):e11.
Brahmer et al., Safety and activity of anti-PD-L1 antibody in ; patients with advanced cancer. N Engl J Med. Jun. 28, 2012;366(26):2455-65.
Brockhoff et al., Receptor agonism and antagonism of dietary bitter compounds. J Neurosci. Oct. 12, 2011;31(41)1 4775-82.
Brown et al., Biophotonic cytotoxicity assay for high-throughput screening of cytolytic killing. J Immunol Methods. Feb. 2005;297(1-2):39-52.
Brunner et al., Quantitative assay of the lytic action of immune lymphoid cells on 51-Cr-labelled allogeneic target cells in vitro; inhibition by isoantibody and by drugs. Immunology. Feb. 1968;14(2):181-96.
Chambers et al., CTLA-4-mediated inhibition in regulation of T cell responses: mechanisms and manipulation in tumor immunotherapy. Annu Rev Immunol. 2001;19:565-94.
Conrad et al., CTLs directed against HER2 specifically cross-react with HER3 and HER4. J Immunol. Jun. 15, 2008;180(12):8135-45.
Dong et al., Tumor-associated B7-H1 promotes T-cell apoptosis: a potential mechanism of immune evasion. Nat Med. Aug. 2002;8(8):793-800.
Gao et al., Advances in the development of cancer immunotherapies. Trends Immunol. Feb. 2013;34(2):90-8.
Gilbert et al., A novel multiplex cell viability assay for high-throughput RNAi screening. PLoS One. 2011;6(12):e28338.
Han et al., Knockdown of RCAS1 expression by RNA interference recovers T cell growth and proliferation. Cancer Lett. Nov. 18, 2007;257(2)182-90.

(Continued)

*Primary Examiner* — John D Ulm
(74) *Attorney, Agent, or Firm* — MH2 Technology Law Group, LLP

(57) ABSTRACT

The present invention relates to a compound selectively binding to a sensory receptor or selectively altering the expression of a sensory receptor for use in a method for treating or preventing a disease associated with a pathologic cellular cytotoxic T cell (CTL) response. Further, the invention relates to means for detecting a sensory receptor for use in a method for diagnosing cellular resistance against CTL response in a patient. The invention further embraces a method for determining the resistance of a cell against a CTL response in vitro and to a method for identifying agents that influence the response of cells to CTLs.

43 Claims, 13 Drawing Sheets

(56) References Cited

OTHER PUBLICATIONS

Hill et al., The flow cytometric analysis of cytokines using multi-analyte fluorescence microarray technology. Methods. Apr. 2006;38(4):312-6.

Meyerhof et al., The molecular receptive ranges of human TAS2R bitter taste receptors. Chem Senses. Feb. 2010;35(2):1 57-70.

Müller et al., Identification of JAK/STAT signalling components by genome-wide RNA interference. Nature. Aug. 11, 2005;436(7052):871-5.

Nishimura et al., Immunosuppressive effects of chloroquine: potential effectiveness for treatment of post-transfusion graft-versus-host disease. Transfus Med. Sep. 1998;8(3):209-14.

Pardoll, The blockade of immune checkpoints in cancer immunotherapy. Nat; Rev Cancer. Mar. 22, 2012;12(4):252-64.

Peng et al., Tumor-associated galectin-3 modulates the function of tumor-reactive T cells. Cancer Res. Sep. 1, 2008;68(17):7228-36.

Rabinovich et al., Immunosuppressive strategies that are mediated by tumor cells. Annu Rev Immunol. 2007;25:267-96.

Slifka et al., Rapid on/off cycling of cytokine production by virus-specific CD8+ T cells. Nature. Sep. 2, 1999;401(6748):76-9.

Solomon et al., Chloroquine and its analogs: a new promise of an old drug; for effective and safe cancer therapies. Eur J Pharmacol. Dec. 2009; 25;625(1-3):220-33.

Strauß et al., Without prior stimulation, tumor-associated lymphocytes from malignant effusions lyse autologous tumor cells in the presence of bispecific antibody HEA125xOKT3. Clin Cancer Res. Jan. 1999;5(1):171-80.

Taniguchi et al., Costunolide and dehydrocostus lactone as inhibitors of killing function of cytotoxic T lymphocytes. Biosci Biotechnol Biochem. Nov. 1995;59(11):2064-7.

Topalian et al., Safety, activity, and immune correlates of anti-PD-1; antibody in cancer. N Engl J Med. Jun. 28, 2012;366(26):2443-54

U.S. Food and Drug Administration. "FDA approves new treatment for a type of late-stage skin cancer." [Press Release]. Mar. 25, 2011. <www.fda.gov/NewsEvents/Newsroom/PressAnnouncements/ucm1193237.htm>.

van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.

Weber, Review: anti-CTLA-4 antibody ipilimumab: case studies of clinical; response and immune-related adverse events. Oncologist. Jul. 2007;12(7):864-72.

Woo et al., Immune inhibitory molecules LAG-3 and PD-1 synergistically regulate T-cell function to promote tumoral immune escape. Cancer Res. Feb. 15, 2012;72(4):917-27.

Yu et al., STATs in cancer inflammation and immunity: a leading role for STAT3. Nat Rev Cancer. Nov. 2009;9(11):798-809.

Zhu et al., Cell surface signaling molecules in the control of immune responses: a tide model. Immunity. Apr. 22, 2011;34(4):466-78.

Zitvogel et al., Immunological aspects of cancer chemotherapy. Nat Rev Immunol. Jan. 2008;8(1):59-73.

Chinese Office Action dated Feb. 5, 2018 for Chinese Patent Application No. 201480047185.X, 16 pages with English translation.

Japanese Office Action dated Apr. 25, 2018 for Japanese Patent Application No. 2016-537284, 15 pages with English translation.

Fig. 10A

Fig. 10B

SEQUENCE LISTING

<160> NUMBER OF SEQ ID NOS: 20

<210> SEQ ID NO 1
<211> LENGTH: 19
<212> TYPE: RNA
<213> ORGANISM: Artificial Sequence
<220> FEATURE:
<223> OTHER INFORMATION: TAS2R3_siRNA s1

<400> SEQUENCE: 1
guaccugccu cccuuaauu          19

<210> SEQ ID NO 2
<211> LENGTH: 19
<212> TYPE: RNA
<213> ORGANISM: Artificial Sequence
<220> FEATURE:
<223> OTHER INFORMATION: TAS2R3_siRNA s2

<400> SEQUENCE: 2
gguagcagcu gguucaaga          19

<210> SEQ ID NO 3
<211> LENGTH: 19
<212> TYPE: RNA
<213> ORGANISM: Artificial Sequence
<220> FEATURE:
<223> OTHER INFORMATION: TAS2R3_siRNA s3

<400> SEQUENCE: 3
ccgcaucucu gaucaauga          19

<210> SEQ ID NO 4
<211> LENGTH: 19
<212> TYPE: RNA
<213> ORGANISM: Artificial Sequence
<220> FEATURE:
<223> OTHER INFORMATION: TASR3_siRNA s4

<400> SEQUENCE: 4
gcagacauuu guagugaug          19

<210> SEQ ID NO 5
<211> LENGTH: 19
<212> TYPE: RNA
<213> ORGANISM: Artificial Sequence
<220> FEATURE:
<223> OTHER INFORMATION: OR51E2_siRNA s1

<400> SEQUENCE: 5
guacaccgcu uuggaaaca          19

<210> SEQ ID NO 6
<211> LENGTH: 19
<212> TYPE: RNA
<213> ORGANISM: Artificial Sequence
<220> FEATURE:
<223> OTHER INFORMATION: OR51E2_siRNA s2

<400> SEQUENCE: 6
gaaacugcau cguggucuu          19

<210> SEQ ID NO 7
<211> LENGTH: 19
<212> TYPE: RNA
<213> ORGANISM: Artificial Sequence

```
<220> FEATURE:
<223> OTHER INFORMATION: OR51E2_siRNA s3

<400> SEQUENCE: 7
caugccaccu uugugcuua                                                  19

<210> SEQ ID NO 8
<211> LENGTH: 19
<212> TYPE: RNA
<213> ORGANISM: Artificial Sequence
<220> FEATURE:
<223> OTHER INFORMATION: OR51E2_siRNA s4

<400> SEQUENCE: 8
ccaauguggu auauggucu                                                  19

<210> SEQ ID NO 9
<211> LENGTH: 19
<212> TYPE: RNA
<213> ORGANISM: Artificial Sequence
<220> FEATURE:
<223> OTHER INFORMATION: PD-L1 first siRNA

<400> SEQUENCE: 9
ugaaaggacu cacuuggua                                                  19

<210> SEQ ID NO 10
<211> LENGTH: 19
<212> TYPE: RNA
<213> ORGANISM: Artificial Sequence
<220> FEATURE:
<223> OTHER INFORMATION: PD-L1   second siRNA

<400> SEQUENCE: 10
cauaguagcu acagacaga                                                  19

<210> SEQ ID NO 11
<211> LENGTH: 19
<212> TYPE: RNA
<213> ORGANISM: Artificial Sequence
<220> FEATURE:
<223> OTHER INFORMATION: PD-L1   third siRNA

<400> SEQUENCE: 11
agaccuggcu gcacuaauu                                                  19

<210> SEQ ID NO 12
<211> LENGTH: 19
<212> TYPE: RNA
<213> ORGANISM: Artificial Sequence
<220> FEATURE:
<223> OTHER INFORMATION: PD-1 forth siRNA

<400> SEQUENCE: 12
ggaccuauau gugguagag                                                  19

<210> SEQ ID NO 13
<211> LENGTH: 19
<212> TYPE: RNA
<213> ORGANISM: Artificial Sequence
<220> FEATURE:
<223> OTHER INFORMATION: RCAS1 first siRNA

<400> SEQUENCE: 13
gaaacuagca gacagagaa                                                  19
```

```
<210> SEQ ID NO 14
<211> LENGTH: 19
<212> TYPE: RNA
<213> ORGANISM: Artificial Sequence
<220> FEATURE:
<223> OTHER INFORMATION: RCAS1 second siRNA

<400> SEQUENCE: 14
ggacggaaau uaaguggag                                              19

<210> SEQ ID NO 15
<211> LENGTH: 19
<212> TYPE: RNA
<213> ORGANISM: Artificial Sequence
<220> FEATURE:
<223> OTHER INFORMATION: RCAS1 third siRNA

<400> SEQUENCE: 15
ggacaugaca ccaacuauu                                              19

<210> SEQ ID NO 16
<211> LENGTH: 19
<212> TYPE: RNA
<213> ORGANISM: Artificial Sequence
<220> FEATURE:
<223> OTHER INFORMATION: RCAS1 forth siRNA

<400> SEQUENCE: 16
gaagcacaac ggcuaauga                                              19

<210> SEQ ID NO 17
<211> LENGTH: 20
<212> TYPE: DNA
<213> ORGANISM: Artificial Sequence
<220> FEATURE:
<223> OTHER INFORMATION: PD-L1 forward primer

<400> SEQUENCE: 17
gtaccttggc tttgccacat                                             20

<210> SEQ ID NO 18
<211> LENGTH: 20
<212> TYPE: DNA
<213> ORGANISM: Artificial Sequence
<220> FEATURE:
<223> OTHER INFORMATION: PD-L1 reverse primer

<400> SEQUENCE: 18
ccaacaccac aaggaggagt                                             20

<210> SEQ ID NO 19
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 19
gagtcaacgg atttggtcgt                                             20

<210> SEQ ID NO 20
<211> LENGTH: 20
<212> TYPE: DNA
<213> ORGANISM: Artificial Sequence
<220> FEATURE:
<223> OTHER INFORMATION: GAPDH reverse primer
```

```
<400> SEQUENCE: 20
ttgattttgg agggatctcg                                                    20
```

CYTOTOXIC T CELL RESPONSE MODIFIERS

CROSS-REFERENCES TO RELATED APPLICATIONS

This application is a national stage entry, filed under 35 U.S.C. § 371, of International Application No. PCT/EP2014/068183, filed on Aug. 27, 2014, and claims the benefit of and priority to U.S. Provisional Application No. 61/870,421, filed Aug. 27, 2013, the entire contents of each of which are hereby incorporated herein by reference in their entireties and for all purposes.

INCORPORATION-BY-REFERENCE OF SEQUENCE LISTING

The contents of the text file named "49839_503N01USSequenceListing.txt", which was created on Feb. 23, 2016, and is 3.93 KB in size, are hereby incorporated by reference in their entireties and for all purposes.

BACKGROUND TO THE INVENTION

The present invention relates to a compound selectively binding to a sensory receptor or selectively altering the expression of a sensory receptor for use in a method for treating or preventing a disease associated with a pathologic cellular cytotoxic T cell (CTL) response. Further, the invention relates to means for detecting a sensory receptor for use in a method for diagnosing cellular resistance against CTL response in a patient. The invention further embraces a method for determining the resistance of a cell against a CTL response in vitro and to a method for identifying agents that influence the response of cells to CTLs.

Today, it is well-known that peripheral immune tolerance plays an important role in several diseases such as in cancer and in preventing autoimmune disorders. In cancer patients, tumor cells often use immune-checkpoints to prevent immune-recognition, thereby imposing resistance against immunotherapy (Rabinovich et al., 2007, and Zitvogel et al., 2006). Successful immunotherapy therefore either depends on an efficient stratification of patients according to the immune sensitivity or resistance of their tumors or on the functional blockade of respective immune-checkpoint pathways (Pardoll, 2012).

Many of the most promising therapeutic strategies in treating diseases associated with immune sensitivity and/or the functional blockade of immune-checkpoint pathways are associated with T cell-based immunotherapy typically involving a cytotoxic T lymphocyte (CTL) response such as exemplarily T cell-based cancer immunotherapy. Current state of the art cancer immunotherapies—involving antigen-specific vaccines or adoptive cellular therapies with tumor-specific CTLs—have meanwhile developed protocols to induce functionally potent T cell responses in the patients (Gao et al., 2013).

However, these therapies are faced with the drawback of cancer cell resistance to specific T cell attack (Rabinovich et al., 2007). Indeed, the success of T cell-based cancer immunotherapy is limited by resistance of many tumors against killing by CTLs.

Therefore, today, there are still a non-negligible number of patients not sufficiently responding to T cell-based immunotherapy.

Neither the reason therefore is known nor a satisfying therapeutic approach overcoming such resistance is available so far. Not even satisfying diagnostic approaches to at least enable the provision of a prognosis on the efficiency of a particular immunotherapy are available so far.

It has been attempted to overcome these problems by unraveling the major immune regulatory pathways imposed by CD80/86-CTLA4 and PDL1-PD1 interactions between the tumor and T cells, respectively (Blank et al., 2004, and Chambers et al., 2001). Blocking antibodies against these surface-expressed proteins can boost anti-tumor immunity and have been successfully applied in clinical trials (Brahmer et al., 2012, Topalian et al., 2012, van Elsas et al., 1999, FDA press release of Mar. 25, 2011 *"FDA approves new treatment for a type of late-stage skin cancer"* and Weber, 2007).

Nevertheless, clinical studies have reported a non-negligible number of unresponsive patients lacking the intratumoral expression of these molecules (Topalian et al., 2012). Indeed, synergistic cooperation between several immune-inhibitory pathways maintain immune tolerance against tumors, which might explain why blocking only one immune-checkpoint node can still result in tumor escape (Berrien-Elliott et al., 2013, and Woo et al., 2012). Still, little is known about molecular factors playing an important role in such immune-inhibitory pathways. One reason is that a comprehensive detection of immune-checkpoint molecules is technically challenging due to the lack of a robust high-throughput assay that enables a qualitative as well as quantitative analysis of heterologous cell-to-cell interaction between the tumor and T cells. So far, only few strategies for identifying such molecular factors playing a role in the impairment of a CTL response have been established in the art that rely on interferon-gamma (IFN-γ) release as an indicator of anti-tumor immune activity (Bellucci et al., 2012, and Hill and Martins, 2006). Furthermore, the methods developed so far are rather insufficient because IFN-γ secretion by immune cells alone does not always correlate with cellular cytotoxicity (Bachmann et al., 1999, and Slifka et al., 1999).

As a consequence, so far, only few molecular factors playing a role in the impairment of a CTL response and few immune suppressive ligands have been identified. Therefore, today, there is still an unmet need for identifying such molecular factors and compounds targeting these as molecular target structures.

BRIEF SUMMARY OF THE INVENTION

Surprisingly, we identified sensory receptors as potent molecular target structures that can regulate or mediate CTL response for diagnosing and treating a pathologic CTL response.

In this context, several compounds serving as potent mediators of a CTL response, in particular for enhancing a CTL response, were identified and a rapid high-throughput screening method that allows a comprehensive identification of such compounds is provided. It could be shown that the identified compounds can serve as a potent medicinal agent for treating and/or diagnosing diseases associated with a pathologic CTL response, in particular as immunosuppressive molecules for treating and/or diagnosing cancer.

DETAILED DESCRIPTION OF THE INVENTION

In a first aspect, the present invention therefore refers to a compound selectively binding to a sensory receptor or selectively altering the expression of a sensory receptor for use in a method for treating or preventing a disease associated with a pathologic cellular cytotoxic T cell (CTL) response.

As used throughout the present invention, the term "compound" may be understood in the broadest sense as any molecule, salt or molecular complex or aggregate that selectively binds to a sensory receptor. The compound may be charged or uncharged, may be soluble or insoluble in water. Preferably, it is at least partly soluble in water. The compound may be or comprise one or more type(s) of small molecules having a molecular weight of not higher than 500 Da, may be or comprise one or more type(s) of high-molecular weight compounds having a molecular weight higher than 500 Da or a mixture thereof.

When used in a therapeutic or diagnostic context—may it be in vivo or in vitro—a compound in the sense of the present invention may also be designated as "medicine", "medicinal compound", "therapeutic", "therapeutic compound", "medicinal agent", "agent", "diagnostic", "diagnostic compound", "diagnostic agent", "diagnostic tool" or the like.

Preferably, the compound is or comprises one or more type(s) of high-molecular weight compounds having a molecular weight higher than 500 Da, more preferably a molecular weight higher than 1 kDa, even more preferably higher than 2 kDa, even more preferably higher than 3 kDa, even more preferably higher than 4 kDa, even more preferably higher than 5 kDa, even more preferably higher than 10 kDa, even more preferably higher than 20 kDa, even more preferably higher than 50 kDa, even more preferably higher than 100 kDa. The compound may or may not comprise amino acid moieties. Highly preferably, the compound mainly comprises amino acid moieties, i.e., is or comprises a polypeptide strand. A polypeptide as used herein may be any compound mainly composed of amino acid moieties connected with another via amide bonds. The number of amino acid moieties comprised in a polypeptide may be from at least three amino acid moieties up to hundreds of amino acid moieties. A polypeptide may also be designated as peptide or protein.

Particularly preferably, the compound according to the present invention is or comprises an antibody or a sensory receptor-binding fragment thereof. Most preferably, the compound according to the present invention is an antibody or a sensory receptor-binding fragment thereof.

Further, the compound according to the present invention may optionally be conjugated or bound to other molecules that may preferably refer to but may not be limited to fusion proteins (e.g., fluorescent proteins), one or more lipid(s) or lipidoid(s), one or more small molecule dye(s) (e.g., fluorescent dyes or UV/Vis dyes (e.g., a p-nitrophenyl moiety, Coomassie Brilliant Blue G-250), one or more quantum dot(s), one or more binding moiety/moieties (e.g., biotin, methotrexate, glycocorticoids or moieties comprising, e.g., one or more active esters, isothiocyanates, maleimides, N-hydroxysuccinimidyl esters, glutaraldehyde derivatives, carbodiimide derivatives or combinations thereof), one or more insoluble and/or soluble polymer(s) (e.g., polyethylene glycol (PEG), hydroxypropyl methacrylate (HPMA), polyethylene imine (PEI)), one or more antibody/antibodies or derivatives thereof (e.g., Fab fragments, single chain antibodies, diabodies, triabodies, flexibodies, tandabs), one or more peptide(s) (e.g., cell-penetrating peptides (CPPs), protein transduction domains (PTDs), signal transduction peptides, etc.), one or more spin label(s), one or more enzyme label(s) (e.g., penicillinase, horseradish peroxidase, alkaline phosphatase), micro- or nanobead(s) (e.g., functionalized silica beads, polysaccharide-based beads), polymersome(s) and/or liposome(s).

Most preferably, the compound is an antibody or a sensory receptor-binding fragment thereof.

As used throughout the invention, the term "antibody" may be understood in the broadest sense as any immunoglobulin (Ig) that enables selective binding to its epitope. In the context of the present invention, the epitope forms part of a sensory receptor, wherein that epitope may be, e.g., a linear or a structural epitope. Typically, an antibody is produced by a B cell or cells derived therefrom (e.g., hybridoma cells). The antibody may be polyclonal or monoclonal, preferably it is a monoclonal antibody. Monoclonal antibodies are well-known by the person skilled in the art as antibodies that are monospecific because they are produced by extensively identical cells that are all progenies, i.e., typically clones, of a common parent cell. In contrast, polyclonal antibodies originate from several different immune cells and typically bind to various epitopes.

As used throughout the invention, a sensory receptor-binding fragment of an antibody may be any polypeptide sequence that originates from an antibody, selectively binds to its epitope, i.e., a sensory receptor, and is typically of shorter length than an antibody. Exemplarily such sensory receptor-binding fragment may be but is not limited to a Fab fragment, a single chain antibody, a diabody, a triabody, a flexibody or a tandab.

Alternatively, the compound may also be a non-antibody polypeptide selectively binding to a sensory receptor, exemplarily, a naturally occurring or artificial binding partner thereof, such as, e.g., a hormone, a cytokine or a polypeptide playing a role in intracellular and/or intercellular signal transduction.

Alternatively, the compound may also be a molecule that is detected by a sensory receptor, such as an olfactory compound recognized by a sensory receptor that functions as an olfactory receptor.

Preferably, the compound selectively binds to one or more extracellular domain(s) of a sensory receptor, i.e., molecular structures present at the outer surface of a cell or binds to a secreted sensory receptor or secreted domains thereof. However, it may be noticed that, alternatively, the compound may optionally also be able to enter cells and, therefore, target intracellular domains of a sensory receptor. This may, exemplarily, be the case when the compound is a small molecule having a molecular weight of not more than 500 Da and an octanol/water distribution coefficient between 1 and 5 and/or when the compound is, independent of its molecular weight, conjugated to or complexed with one or more uptake mediator(s) selected from, e.g., a cell-penetrating peptide (CPP), a protein transduction domain (PTD), a signal transduction peptide, a positively charged and/or amphiphilic compound (e.g., a positively charged and/or amphiphilic fatty acid), a positively charged polymer (e.g., polyethylene imine (PEI), a polymer comprising guanidinium moieties), an amphiphilic peptide or polymer, a micelle and/or a liposome.

The person skilled in the art will notice that an interfering RNA as well as a sensory receptor-blocking antibody are particularly preferred agents when the CTL response is intended to be strengthened, whereas a T cell-sensory receptor crosslinking antibody may be a particularly preferred agent when the CTL response is intended to be decreased.

As used throughout the invention, the term "selectively binding to a sensory receptor" may be understood in the broadest sense as the formation of a specific rather stable interaction between the "Binding", as used herein, may be covalent or non-covalent binding, preferably non-covalent binding. The person skilled in the art will know that in the formation of a non-covalent binding, beside others, the formation of hydrogen bonds and electrostatic bonds, van der Waals forces, hydrophobic forces and Π-Π electron interaction may play a role. As used in the context of the present invention, binding is preferably the formation of an interaction having a dissociation equilibrium constant ($k_d$) of below 10 µM, below 1 µM, below 100 nM, below 10 nM or even below 1 nM.

As used herein, "selectively binding" means that the binding is specific for a particular molecular target, i.e., a particular sensory receptor, or a group of particular molecular targets such as, e.g. a particular class or subclass of sensory receptors. Therefore, preferably, the binding affinity to the particular molecular target or the particular group of particular molecular targets has an at least 5-fold, at least 10-fold, at least 20-fold, at least 50-fold, at least 100-fold, at least 200-fold, at least 500-fold, at least 1000-fold, at least 2000-fold, at least 5000-fold, at least 10000-fold, at least $10^5$-fold or even at least $10^6$-fold affinity than to other targets, i.e., exemplarily other polypeptides, in particular other membrane associated receptors.

The term "selectively altering the expression of a sensory receptor" may be understood in the broadest sense as inducing or provoking any specific change in the production of a sensory receptor.

"Expression" as used herein means, in its broadest sense, the production of a sensory receptor that may enable specific interaction with a CTL. This interaction may be direct interaction between the sensory receptor and the CTL or may be indirect interaction between the sensory receptor and the CTL, optionally, via one or more (soluble) receptor(s). Therefore, expression may include transcription and translation and, optionally splicing and posttranslational modification(s). Any of these steps may or may not be influenced by the compound.

As used herein "altering the expression" means that the rate of expression of a sensory receptor is changed in comparison to that of in a comparable cell cultivated under comparable conditions but not contacted with the compound.

Preferably, altering the expression of a sensory receptor is reducing the expression of a sensory receptor. Then, preferably, the compound is an interfering ribonucleic acid (iRNA or RNAi) molecule (also known as silencing RNA). Throughout the present invention, an interfering RNA is preferably small interfering ribonucleic acid (siRNA) or small hairpin RNA (shRNA), or a RNA analogue functioning like an interfering RNA. The person skilled in the art will notice that an siRNA in the context of the present invention will typically be complementary to a messenger ribonucleic acid (mRNA) encoding for a sensory receptor of interest.

However, the compound according to the present invention may also be another compound such as, e.g., a small molecule that has a decreasing influence on the production of the functional form of sensory receptor, such as, e.g., a hormone or cytokine either having an influence on signal transduction or a cell-penetrating hormone or cytokine interfering in the expression of a sensory receptor. It will be noticed that when administered to a subject in vivo, the compound, in particular when it is an RNA or analogue thereof, will typically be stabilized against degradation, such as, e.g., by inclusion in liposomes or polymersomes, by conjugation or complexation to soluble polymers, by inclusion in or conjugation to microbeads or nanobeads or complexation with one or more amphiphilic agent(s).

Alternatively, altering the expression of a sensory receptor may also be increasing the expression of a sensory receptor. Then, preferably, the compound is or comprises genetic material encoding for a sensory receptor, in particular deoxyribonucleic acid (DNA) encoding for a sensory receptor. However, it may also be another compound such as, e.g., a small molecule that has a positive influence on the production of the functional form of sensory receptor, such as, e.g., a hormone or cytokine either having an influence on signal transduction or a cell-penetrating hormone or cytokine interfering in the expression of a sensory receptor.

As used herein, "selectively altering the expression" means that the rate of expression of a particular sensory receptor or a group of particular sensory receptors of interest such as, e.g. a particular class or subclass of sensory receptors is specifically changed. Therefore, preferably, the expression of the particular sensory receptor or particular group of sensory receptors in a cell is at least 5%, at least 10%, at least 20%, at least 30%, at least 40%, at least 50%, at least 60%, at least 70%, at least 80%, at least 90%, at least 100%, at least 150%, at least 200%, at least 300%, at least 500% or even at least 1000% amended in comparison to a comparable cell cultivated under comparable conditions but not contacted with the compound.

The compound selectively binding to a sensory receptor or selectively altering the expression of a sensory receptor as used herein may also be or comprise genetic material encoding for:

(i) a compound selectively binding to a sensory receptor; and/or
(ii) a compound selectively altering the expression of a sensory receptor.

As used throughout the present invention, the term "genetic material" may be understood in the broadest sense as any material enabling the conveyance of genetic information to be expressed such as, exemplarily but not limited to deoxyribonucleic acid (DNA), ribonucleic acid (RNA), peptide nucleic acid (PNA), morpholino-locked nucleic acid (LNA), as well as glycol nucleic acid (GNA) and threose nucleic acid (TNA), 2'-O-methyl-substituted RNA or a combination of two or more thereof. Genetic material may optionally form part of a greater molecule and/or may be complexed by one or more other molecule(s). The genetic material may have or be comprised in a molecule having linear structure or circular structure. Genetic material may optionally form part of a vector. The person skilled in the art will be familiar with numerous suitable vectors such as, e.g., a virus or viroid, a plasmid, a prokaryote (e.g., a bacterium) and/or a eukaryotic cell (e.g., a plant, fungal (e.g., yeast) or animal cell (e.g. mammalian or insect cell). It will be noticed that when administered to a subject in vivo, the genetic material will typically be stabilized against degradation, such as, e.g., by inclusion in liposomes, polymersomes, by conjugation or complexation to soluble polymers, by inclusion in or conjugation to microbeads or nanobeads, inclusion in a virus or viroid, or complexation with one or more amphiphilic agent(s).

Most preferably, the compound is an antibody, in particular a monoclonal antibody, selectively binding to a particular sensory receptor or a group of sensory receptors.

All the aforementioned types of compounds may be used in a method for treating a disease associated with a pathologic cellular CTL response.

The term "cytotoxic T cell" and its abbreviation "CTL" as used herein may be understood in the broadest sense as any T lymphocyte that is able to induce cell death, in particular in neoplastic cells, cells that are infected, particularly viruses-infected cells, and/or cells in other pathologic conditions. In this context, the terms "cytotoxic T cell", "CTL", "cytotoxic TC", "cytotoxic T lymphocyte", "T killer cell", "cytolytic T cell" and "killer T cell" may be understood interchangeably. The cytotoxic T cell may be a cytotoxic CD8+ T cell. Typically, a CTL in the context of the present invention has at least one T cell receptor (TCR) on its surface that enables the recognition of particular molecular structures presented at surfaces of other cells. Those molecular structures will typically be antigens presented at the surface of the other cell in complex with major histocompatibility complex (MHC) class I, where they can be recognized by the CTL. If the TCR is specific for that antigen, it will bind to said complex of the MHC class I with the antigen and a CTL response occurs, i.e., the other cell is destroyed. Preferably, the CTLs used in the context of the present invention are mammalian CTLs, in particular human CTLs, so that the CTL response is a human CTL response.

It will be apparent that the cell may form part of a tissue. Then, a diseased tissue may be treated. The tissue may form part of an organ. Then, the diseased organ may be treated. Herein, the term "treating" may be understood in the broadest sense as subjecting a subject to any medicinal or non-medicinal therapy, wherein such therapy is preferably a medicinal therapy and the subject is a patient having a pathological CTL response.

Herein, the term "preventing" may be understood in the broadest sense as subjecting a subject to any medicinal or non-medicinal therapy, protecting the subject of developing such pathological CTL response, wherein such therapy is preferably a medicinal therapy and the subject is a patient being at risk of developing a pathological CTL response.

As used in the context of the present invention, the term "patient" may be understood in the broadest sense as any subject whom the compound is administered to, irrespective of whether it is a human or an animal and whether clinical symptoms occur or do not occur. Preferably, the patient is a human patient. Preferably, the patient has developed a pathological CTL response and/or is at risk of developing a pathological CTL response.

The term "disease" as used throughout the invention may be understood in the broadest sense as any pathological condition wherein a pathologic cellular CTL response occurs irrespective of whether clinical symptoms occur or do not occur. A pathological condition is any condition that differs from the healthy condition.

When a cellular CTL response occurs, this typically results in the death of the cell contacted with the CTL. The cell used in the context of the present invention may be any cell that can be involved in a CTL response, i.e., preferably cells of mammalian origin, in particular cells of human origin. Most preferably, the cells are involved in abnormal growth cells such as, e.g., neoplastic cells, in particular cancer cells. Then tumor resistance may be mediated.

When a CTL response is too weak, pathologic cells may erroneously not be removed (killed), such as, e.g., neoplastic cells or infected cells. Then, exemplarily, neoplasia, in particular cancer, may occur or infections may be promoted.

On the contrary, when a CTL response is too strong, cells may be killed that are not intended to be killed, i.e., typically also healthy cells. Then, exemplarily, an autoimmune disease may occur wherein healthy cells are killed and tissue is erroneously harmed or when tissue or a whole organ is transplanted from a graft into a host patient, said tissue or organ is rejected unwantedly (graft-versus-host disease).

Accordingly, in a preferred embodiment, the disease to be treated is selected from the group consisting of neoplasia, in particular cancer, an autoimmune disease, an infection and graft-versus-host disease.

As used herein, neoplasia may be understood in the broadest sense as any formation of new tissue, in particular abnormal formation of novel tissue mass, typically resulting from an abnormal division rate of particular cells. It may also include early stages of neoplasia such as, e.g., metaplasia or dysplasia. Neoplasia may or may not be dependent on external stimuli influencing the cellular division rate and tissue growth. Neoplasia may be benign, pre-malignant (cancerous tissue in situ) or malignant (cancer). Cancer may include all cancerous cells, i.e., the cells forming part of a tumor mass and/or one or more metastasis/metastases.

A cancer in the context may be any type of cancer known in the art. It may be cancer forming or not forming solid tumors, preferably cancer forming or not forming solid tumors. Exemplarily, cancer may include but may not be limited to carcinoma (cancer derived from epithelial cells, such as, e.g., breast, prostate, lung, pancreas, and colon cancer), sarcoma (cancers derived from connective tissue, typically from a mesenchymal cell, such as, e.g., bone, cartilage, fat, or nerve cell cancer), lymphoma and leukemia (cancers derived from hematopoietic cells, such as, e.g., blood cancer), seminoma/dysgerminoma (germ cell tumor, cancer derived from pluripotent cells, such as, e.g, testicle or ovary cancer), melanoma and blastoma (cancers derived from immature precursor cells or embryonic tissue). Preferably, the cancer is carcinoma, sarcoma, seminoma/dysgerminoma, melanoma (cancer derived from skin cells) or blastoma. Even more preferably, the cancer is a carcinoma, in particular breast cancer.

An autoimmune disease typically arises from an inappropriate immune response of the body against substances and tissues normally present in the body (autoimmunity). This may be restricted to certain organs or involve one or more tissue(s) in different places An infection in the context of the present invention is any infection known in the art, preferably a viral infection, in particular a viral infection wherein the immune system malfunctions, i.e., overreacts (e.g., some forms of influenza) or reacts to weak (human immune deficiency virus (HIV) infections, herpes, warts).

As used herein, "graft-versus-host disease" or "GVHD" may me understood in the broadest sense as the common complication following an allogeneic tissue transplant particularly, but not only, occurring in the context of stem cell or bone marrow transplants but also occurring in the context of other forms of tissue graft.

Most preferably, a disease in the context of the present invention is cancer, in particular a solid cancer such as breast cancer.

As used throughout the present invention. The term "sensory receptor" may be understood in the broadest sense as any molecular structure that enables recognition of environmental influences, in particular wherein said environmental influences are the presence of particular chemical compounds (olfactory receptors) and/or physical influences such as, e.g., light irradiation (photoreceptors), temperature or mechanic influences such as, e.g., touch/pressure (mechanoreceptors). In the context of the present invention, in particular sensory receptor recognizing the presence of particular chemical compounds (i.e., chemical senses) or light irradiation play a major role. A sensory receptor, in the context of the present invention may function as an immune-checkpoint molecule.

Preferably, a sensory receptor in the context of the present invention mainly comprises one or more polypeptide strand(s). However, it will be noticed that it may optionally further comprise cofactors such as, e.g., opsin, and/or may optionally further comprise retinal. Further, many of the co-factors may be associated with G proteins and/or may function as calcium channels.

Most preferably, a sensory receptor in the context of the present invention may be a G protein-coupled receptor (GPCR), in particular wherein said GPCR is a receptor belonging to the rhodopsin-like family of GPCRs, most particularly wherein it is a class A rhodopsin-like family of G protein-coupled receptors (GPCRs).

In a preferred embodiment, the sensory receptor is a receptor localized at the cellular surface, preferably wherein said sensory receptor is selected from the group consisting of (a) an olfactory receptor, preferably selected from the group consisting of:
  (i) a taste receptor, in particular a taste receptor type 2 (TAS2R), in particular taste receptor type 2 member 3 (TAS2R3),
  (ii) an olfactory receptor of family 1, 2 or 51, in particular an olfactory receptor of family 1 subfamily F (OR1F), in particular an olfactory receptor of family 1 subfamily F member 1 (OR1F1), an olfactory receptor of family 2 subfamily J (OR2J), in particular an olfactory receptor of family 2 subfamily J member 2 (OR2J2), or an olfactory receptor of family 51 subfamily E (OR51E), in particular an olfactory receptor of family 51 subfamily E member 2 (OR51E2), and
  (iii) a vomeronasal receptor, preferably vomeronasal 1, in particular vomeronasal 1 receptor 4 (VN1R4);
  (iv) a pheromone receptor; and
(b) an opsin, in particular opsin 3 (OPN3).

The term "at the cellular surface" means that the receptor may comprise one or more transmembrane domain(s), may be partly or entirely integrated in the plasmamembrane and/or may be associated with the membrane or with polypeptides comprising one or more transmembrane domain(s) and/or partly or entirely integrated in the plasmamembrane. Therefore such sensory receptor may also be designated as "surface receptor".

As used throughout the present invention, the terms "olfactory receptor", "odor receptor", "taste receptor", and "gustatory receptor" may be understood interchangeably as any receptor enabling a taste and/or smell perception known in the art. It is widely known that for many compounds, taste and smell are recognized by the same receptors and are not entirely separable in perception also. Therefore, these two perceptions are recognized by a unique group of receptors. Exemplarily, an olfactory receptor may be a taste receptor type 2 (TAS2R), in particular taste receptor type 2 member 3 (TAS2R3). In this context the terms "taste receptor type 2", "taste receptor of family 2" and "TAS2R" may be understood exchangeably. Exemplarily, it may be an olfactory receptor of family 1 subfamily F (OR1F), in particular an olfactory receptor of family 1 subfamily F member 1 (OR1F1), an olfactory receptor of family 2 subfamily J (OR2J), in particular an olfactory receptor of family 2 subfamily J member 2 (OR2J2) or an olfactory receptor of family 51 subfamily E (OR51E), in particular an olfactory receptor of family 51 subfamily E member 2 (OR51E2). Exemplarily, it may be a vomeronasal receptor, preferably vomeronasal 1, in particular vomeronasal 1 receptor 4 (VN1R4) or a pheromone receptor.

In a preferred embodiment, the compound enhances an immune response to an activated CTL, in particular in a patient suffering from a neoplasia, in particular cancer, preferably wherein the local surface concentration and/or T cell-binding activity of the surface receptor that prevents CTL response is reduced.

Herein, a reduction of the activity of the surface receptor may be the result from a reduced expression of sensory receptors, a reduced local concentration of receptors and/or blockage of the receptor by means of blocking the T cell interaction side of said receptor by either binding a compound thereto and/or by reducing its binding affinity by allosterically amending the T cell interaction side. Most preferably, the binding side is blocked by binding a compound, such as, in particular an antibody to the respective sensory receptor.

Accordingly, in a preferred embodiment, the compound according to the present invention is selected from the group consisting of:
(i) a compound reducing the expression of a sensory receptor, preferably an interfering RNA, in particular a small interfering ribonucleic acid (siRNA) or a small hairpin RNA (shRNA), complementary to mRNA encoding for said sensory receptor, and
(ii) a compound preventing the T cell-binding activity to said sensory receptor, in particular wherein said compound is an antibody or a sensory receptor-binding fragment.

As mentioned above, also the opposite, i.e., the enhancement on sensory receptor-T cell interaction may have a beneficial therapeutic effect, in particular when a suppression of the CTL response is intended.

Therefore, in an alternative preferred embodiment, the compound suppresses an immune response to an activated CTL, in particular in a patient suffering from an autoimmune diseases and/or graft-versus-host disease, preferably wherein the amount and/or T cell-binding activity of the surface receptor that prevents CTL response is enhanced.

In an even more preferred embodiment, the compound is then selected from the group consisting of:
(i) genetic material encoding for a sensory receptor,
(ii) a compound enhancing the expression of said sensory receptor, and
(iii) a compound cross-linking a surface polypeptide preventing CTL with a T cell, in particular a cross-linking antibody or antibody fragment.

When an enhancement of a CTL response as well as when a suppression of a CTL response is intended, the compound according to the present invention may be either used as the sole medicinal agent or may be combined with one or more further immunomodulatory compound(s) involved in one or more immune-inhibitory pathway(s) and, thereby, being part of the "immune modulatome".

In a preferred embodiment, the compound is used in combination with one or more further immunomodulatory compound(s).

Exemplarily, such further immunomodulatory compound may be an interleukin (e.g., IL-2, IL-4, IL-7, IL-10, IL-12, IL-13), a cytokine (e.g., an interferon, G-CSF, imiquimod), a chemokine (e.g., CCL3, CCL26, CXCL7), cytosine phosphate-guanosine, an oligodeoxynucleotide, a glucan, a glucocorticoid, an immunosuppressive antibody and/or tumor necrosis factor alpha (e.g., TNFα).

It will be understood that the present invention also relates to a pharmaceutical composition and a kit comprising the compound according to the present invention and/or means for detecting according to the present invention as well optionally further comprising (i) one or more pharmaceutically acceptable carrier(s) and/or (ii) a user manual.

In the context of the present invention, the term "kit" may be understood in the broadest sense as a composition of different products that may be used for performing a claimed therapy. The kit may comprise means for detecting according to the present invention (i.e., detecting a sensory receptor), pharmaceutically acceptable carriers, a user manual, syringes, needles, etc. Optionally, the means may be dissolved or may be freeze-dried.

As used herein, the term "pharmaceutically acceptable carrier" may refer to any substance that may support the pharmacological acceptance of the means. The means may be administered orally or may be injected. It may be pharmaceutically formulated in a dry form (e.g., as a powder, a tablet, a pill, a capsule, a chewable capsule, etc.) or as a liquid (e.g., a spray, a syrup, a juice, a gel, a liquid, a paste, an injection solution, etc.) A pharmaceutically acceptable carrier may be a solvent with no or low toxicity such as, e.g., water, dimethyl sulfoxide (DMSO), ethanol, vegetable oil, paraffin oil or combinations thereof. Furthermore, the pharmaceutically acceptable carrier may contain one or more detergent(s), one or more foaming agent(s) (e.g., sodium lauryl sulfate (SLS)/sodium doceyl sulfate (SDS)), one or more coloring agent(s) (e.g., $TiO_2$, food coloring), one or more vitamin(s), one or more salt(s) (e.g., sodium, potassium, calcium, zinc salts), one or more humectant(s) (e.g., sorbitol, glycerol, mannitol, propylenglycol, polydextrose), one or more enzyme(s), one or more preserving agent(s) (e.g., benzoic acid, methylparabene), one or more texturing agent(s) (e.g., carboxymethyl cellulose (CMC), polyethylene glycol (PEG), sorbitol), one or more emulsifier(s), one or more bulking agent(s), one or more glacing agent(s), one or more separating agent(s), one or more antioxidant(s), one or more herbal and plant extract(s), one or more stabilizing agent(s), one or more polymer(s) (e.g., hydroxypropyl methacrylamide (HPMA), polyethylene imine (PEI), carboxymethyl cellulose (CMC), polyethylene glycol (PEG)), one or more uptake mediator(s) (e.g., polyethylene imine (PEI), dimethyl sulfoxide (DMSO), a cell-penetrating peptide (CPP), a protein transduction domain (PTD), an antimicrobial peptide, etc.) one or more antibody/antibodies, one or more sweetener(s) (e.g., sucrose, acesulfam K, saccharin Na), one or more counterstain dye(s) (e.g., fluorescein, fluorescein derivatives, Cy dyes, an Alexa Fluor dyes, S dyes, rhodamine, quantum dots, etc.), one or more homeopathic ingredient(s), one or more gustatory substance(s) and/or one or more fragrance(s).

The present invention not only relates to therapeutic approaches based on the modulation of CTL response by sensory receptors, but also relates to diagnosis of cellular resistance against CTL response based on the same inventive concept.

Accordingly, in a further aspect, the present invention refers to means for detecting a sensory receptor for use in a method for diagnosing cellular resistance against CTL response in a patient.

Such method, beside other applications, enables prognosing the usefulness of a T cell-based, in particular a CTL-based, therapy. When a CTL response is desired (e.g., in a cancer patient or a patient suffering from an infectious disease) and it is found that the patient or a particular tissue therein reveals a rather strong resistance against a CTL response, the artisan treating said patient may preferably consider treating the patient also with a compound reducing the resistance against CTL response. This may preferably be a compound according to the present invention. Alternatively or additionally, the artisan may use other than CTL-based methods to treat the patient. On the contrary, when a CTL response is too strong or erroneously occurring (e.g., in an autoimmune diseased patient or a patient suffering from a graft-versus-host disease), the artisan treating said patient may preferably consider treating the patient also with a compound increasing the resistance against CTL response. This may preferably be a compound according to the present invention.

The term "means for detecting" may be understood in the broadest sense as any compound(s) or composition suitable for detecting a sensory receptor. Exemplarily the means may be or comprise a compound selectively binding to the sensory receptor.

As used herein, the term "compound" may be understood in the broadest sense as defined above for the compound according to the present invention.

The means for detecting may be or comprise one or more type(s) of small molecules having a molecular weight of not higher than 500 Da, may be or comprise one or more type(s) of high-molecular weight compounds having a molecular weight higher than 500 Da or a mixture thereof. Preferably, the means for detecting are or comprise one or more type(s) of high-molecular weight compounds. In a particularly preferred embodiment, the means for detecting are or comprise one or more antibody/antibodies or derivatives thereof (e.g., Fab fragments, single chain antibodies, diabodies, triabodies, flexibodies, tandabs) selectively binding to a sensory receptor.

Alternatively, the means may also be the natural or artificial specific binding partners of a sensory receptor, such as, e.g., a hormone or an olfactory compound specifically recognized by one of the olfactory receptors.

It will be noticed that, in particular for in vivo applications, such high-molecular weight compound preferably specifically binds to a molecular structure of a sensory receptor, wherein said molecular structure is present at the outer surface of a cell. Typically, said molecular structure present at the outer surface of a cell is an extracellular domain or a combination of two or more extracellular domains of a sensory receptor. When the high-molecular weight compound is an antibody or fragment thereof, such molecular structure is an epitope and may be, e.g., a linear or a structural epitope.

Preferably, in order to improve detectability, the means or parts thereof are labeled, in particular fluorescently labeled, labeled by a contrast agent, spin-labeled and/or radioactively labeled, in particular wherein said compound is an antibody or a sensory receptor-binding fragment thereof.

As used herein the term "detecting" may be understood in the broadest sense as any recognition, determination, localization and/or quantification of a sensory receptor. Detecting as used herein may be performed by any means known in the art.

In the context of this aspect of the present invention, preferably, detecting is performed in the patient in vivo. Alternatively or additionally, in the context of this aspect of the present invention, detecting may also be performed in a sample in vitro, preferably, wherein said sample is obtained from the patient. Detecting as used herein may be performed by any means known for this purpose in the art such as, e.g., by means of X-ray-based techniques (e.g., standard X-ray, computer tomography (CT)), spin detection (e.g., Magnetic Resonance Imaging (MRI)), by detecting fluorescence and/or other light emission (e.g., by Fluorescent Molecular Tomography (FMT), Fluorescence Molecular Imaging (FMI), Single Photon Emission Computed Tomography (SPECT), light microscopy (bright field microscopy), fluorescence microscopy (e.g., fluorescence light microscopy, confocal microscopy (e.g., laser scanning microscopy (LSM), single photon microscopy)), fluorescence correlation spectroscopy (FCS), fluorescence cross-correlation spectroscopy (FCCS), fluorescence depolarization), by detecting radioactivity (e.g., Positron Emission Spectroscopy (PET), scintigraphy), electron microscopy and/or by detecting ultrasound. It will be understood by a person skilled in the art that two or more of the above methods may also be combined with another.

The person skilled in the art will notice that, for many of the detecting techniques described above, it will be beneficial to label the means according to the intended detection method to improve their detectability. Exemplarily, fluorescently labeled means may be used for fluorescence-based methods, whereas spin-labeled means may be used for spin detection, radioactively labeled means may be used for detection of radioactivity and heavy atom-labeled means may be used for X-ray-based methods and electron microscopy.

Further, the means may be conjugated or bound to other molecules that may preferably refer to but may not be limited to fusion proteins (e.g., fluorescent proteins), one or more lipid(s) or lipidoid(s), one or more small molecule dye(s) (e.g., fluorescent dyes or UV/Vis dyes (e.g., a p-nitrophenyl moiety, Coomassie Brilliant Blue G-250), one or more quantum dot(s), one or more binding moiety/moieties (e.g., biotin, methotrexate, glycocorticoids or moieties comprising, e.g., one or more active ester(s), isothiocyanate(s), maleimide(s), N-hydroxysuccinimidyl ester(s), glutaraldehyde derivative(s), carbodiimide derivative(s) or combinations thereof), one or more insoluble and/or soluble polymer(s) (e.g., polyethylene glycol (PEG), hydroxypropyl methacrylate (HPMA), polyethylene imine (PEI)), one or more antibody/antibodies or derivatives thereof (e.g., Fab fragments, single chain antibodies, diabodies, triabodies, flexibodies, tandabs), one or more peptide(s) (e.g., cell-penetrating peptides (CPPs), protein transduction domains (PTDs), signal transduction peptides, etc.), one or more spin label(s), one or more enzyme label(s) (e.g., penicillinase, horseradish peroxidase, alkaline phosphatase), micro- or nanobead(s) (e.g., functionalized silica beads, polysaccharide-based beads), polymersome(s) and/or liposome(s).

When the method is performed in vitro, the sample may optionally be fixed and/or stained and may also be designated as "specimen" or "microscopic specimen". When labeled or unlabeled means have been administered to said patient, samples of cells or solid tissue may be examined by any immunological method (e.g., enzyme-lined immunosorbent assay (ELISA), flow cytometry, Western Blot, FCS and/or FCCS).

It will be understood that the present invention also relates to a pharmaceutical composition and a kit comprising the means for diagnosing according to the present invention as well as optionally further comprising (i) one or more pharmaceutically acceptable carrier(s) and/or (ii) a user manual.

In a preferred embodiment, the means comprise at least one compound selectively binding to the sensory receptor, preferably wherein said compound is labeled, in particular fluorescently labeled, labeled by a contrast agent, spin-labeled and/or radioactively labeled, in particular wherein said compound is an antibody or a sensory receptor-binding fragment thereof.

In the context of the present invention, the term "labeled" may be understood in the broadest sense as means that carry one or more moiety/moieties that enable(s) the detection thereof in vivo and/or in vitro. As used herein the terms "label", "detectable moiety" and "marker" may be understood interchangeably. The label may be, e.g., a radioactive label, spin label, a fluorescent label or a luminescent label. The label may be conjugated to the means directly or via a functional linker, (e.g., a peptide linker, a polyethylene glycol (PEG) linker, a saccharide linker, a fatty acid linker, an alkyl linker, etc.). Alternatively, one or more labeled antibody/antibodies or derivatives thereof (e.g., Fab fragments, single chain antibodies, diabodies, triabodies, flexibodies, tandabs) may be labeled and bound to the means. The binding to the means may occur in vitro or in vivo. Aforementioned labels may be added to the means in vitro or directly in the patient in vivo.

In the context of the present invention, a radioactive label may include but may not be limited to $^{3}H$, $^{32}P$, $^{35}S$, $^{14}C$, $^{99m}Tc$ or lanthonoids (e.g., $^{64}Gd$) suitable for scintillation assays, computer tomography (CT) or a label suitable for Positron Emission Tomography (PET). The means themselves may be directly labeled radioactively or via the conjugation or complexation of a radioactively labeled molecule. Moreover, the means may be labeled by means of a spin label, such as one or more heavy isotope(s), e.g., $^{13}C$, Gd or $^{2}H$ detectable by Nuclear Magnetic Resonance (NMR).

The label may also be a fluorescent dye or a luminescent dye. As used herein, the terms "fluorescent dye", "fluorescence dye" and "fluorophore" may be used interchangeably. A fluorescent dye may be a fluorescent polypeptide (e.g., cyan fluorescent protein (CFP), green fluorescent protein (GFP) or yellow fluorescent protein (YFP), red fluorescent protein (RFP), mCherry, etc.), a small-molecule dye (e.g., a Cy dye (e.g., Cy3, Cy5, Cy5.5, Cy 7), an Alexa dye (e.g., Alexa Fluor 488, Alexa Fluor 546, Alexa Fluor 647, Alexa Fluor 680, Alexa Fluor 750), a Visen dye (e.g. VivoTag680, VivoTag750), an S dye (e.g., S0387), a DyLight fluorophore (e.g., DyLight 750, DyLight 800), an IRDye (e.g., IRDye 680, IRDye 800), a fluorescein dye (e.g., fluorescein, carboxyfluorescein, fluorescein isothiocyanate (FITC)), a rhodamine dye (e.g., rhodamine, tetramethylrhodamine (TAMRA)) or a HOECHST dye) or a quantum dot. One or more dye(s) may be combined. As used herein, the term "luminescent dye" may refer to every molecule that emits light upon a chemical or a biochemical reaction.

In this context referring to a diagnostic method, the term "sensory receptor" may be understood in the broadest sense as defined above.

Accordingly, in a preferred embodiment, the sensory receptor is a receptor localized at the cellular surface, preferably wherein said sensory receptor is selected from the group consisting of (a) an olfactory receptor, preferably selected from the group consisting of:
(i) a taste receptor, in particular a taste receptor type 2 (TAS2R), in particular taste receptor type 2 member 3 (TAS2R3),
(ii) an olfactory receptor of family 1, 2 or 51, in particular an olfactory receptor of family 1 subfamily F (OR1F), in particular an olfactory receptor of family 1 subfamily F member 1 (OR1F1), an olfactory receptor of family 2 subfamily J (OR2J), in particular an olfactory receptor of family 2 subfamily J member 2 (OR2J2), or an olfactory receptor of family 51 subfamily E (OR51E), in particular an olfactory receptor of family 51 subfamily E member 2 (OR51E2), and
(iii) a vomeronasal receptor, preferably vomeronasal 1, in particular vomeronasal 1 receptor 4 (VN1R4);

(iv) a pheromone receptor; and
(b) an opsin, in particular opsin 3 (OPN3).

The terms used in this context may be understood in the broadest sense as defined above.

Also in the context of diagnosing, in a preferred embodiment, the patient is suffering from a neoplasia, an autoimmune disease, an infection and/or a graft-versus-host disease, in particular wherein said patient is suffering from a neoplasia, in particular wherein said neoplasia is cancer, particularly breast cancer.

The terms used in this context may be understood in the broadest sense as defined above.

It will be understood that the present invention also relates to a kit comprising the means for detecting according to the present invention as well optionally further comprising (i) one or more pharmaceutically acceptable carrier(s) and/or (ii) a user manual.

In the context of the present invention, the term "kit" may be understood in the broadest sense as a composition of different products that may be used for performing a diagnosis. The kit may comprise the contents as described in the context of therapy above.

The present invention not only refers to a diagnostic method in a patient in vivo, but also in vitro. Accordingly, in a further aspect, the present invention relates to a method for determining the resistance of a cell against a CTL response in vitro, said method comprising the steps:
(i) providing the cell to be tested for resistance against a CTL response,
(ii) determining the amount of at least one sensory receptor at the surface of said cell, and
(iii) comparing said amount of the sensory receptor with a standard of a comparable cell lacking the sensory receptor at its surface and/or a comparable cell having such amounts at its surface that an extensive resistance to a CTL response occurs.

As used in the context of the present invention, the terms "in vitro" and "ex vivo" may be understood interchangeably in the broadest sense as any method performed outside the living body of a multicellular organism such as, e.g., a human patient. An in vitro method may be a method performed outside of any living material and/or may be performed in cell culture, egg-based methods or any other method considered as an in vitro method by those skilled in the art and/or in case law of one or more jurisdiction(s), such as, e.g., the one or more of the member state(s) of the European Patent Convention (EPC) and/or the U.S.A. An in vitro method may also be designated as "assays", "screening assay", "screening" or the like.

In the first step, the cell to be tested for resistance against a CTL response is provided. Herein, the term "providing the cell" may be understood in the broadest sense as obtaining the cell to be tested from any source suitable therefore. Preferably, the cell is obtained from a patient. This may include that the cell is obtained from a patient directly, or is passaged one or more often after being extracted from a patient. Alternatively, the cell may also be a cell obtained from a cell culture. In any case, the cell is preferably a eukaryotic cell, in particular a mammalian cell. Most preferably, the cell is a human cell.

The CTL response is most preferably a CTL response from the same organism the cell is obtained from. The CTL also used in the context of this method is defined in the context of therapy above.

In a further step, the amount of at least one sensory receptor at the surface of the cell is determined. Here, determining the amount of at least one sensory receptor at the surface of the cell may be performed by any means known in the art and defined above, in particular, by means of labeled antibodies as defined above.

Alternatively or additionally, detection may also be performed at the gene expression level, e.g., by using qPCR primer probes. Then, exemplarily, reverse transcription and quantitative PCR may be performed. qPCR primer probes may then serve as diagnostic tools as well and may provide information on the cell interior.

Finally, the amount of the sensory receptor on the surface of the cell is compared with a standard sample. Typically, this standard sample comprises a comparable cell lacking the sensory receptor at its surface (positive control (Ctrl) of CTL response) and/or a comparable cell having such amounts at its surface that an extensive resistance to a CTL response occurs (negative control (Ctrl) of CTL response).

A particularly preferred embodiment of this method is defined in detail in the examples of the present invention.

Also in this context, in a preferred embodiment, the sensory receptor is a receptor localized at the cellular surface, preferably wherein said sensory receptor is selected from the group consisting of
(a) an olfactory receptor, preferably selected from the group consisting of:
  (i) a taste receptor, in particular a taste receptor type 2 (TAS2R), in particular taste receptor type 2 member 3 (TAS2R3),
  (ii) an olfactory receptor of family 1, 2 or 51, in particular an olfactory receptor of family 1 subfamily F (OR1F), in particular an olfactory receptor of family 1 subfamily F member 1 (OR1F1), an olfactory receptor of family 2 subfamily J (OR2J) in particular an olfactory receptor of family 2 subfamily J member 2 (OR2J2), or an olfactory receptor of family 51 subfamily E (OR51E), in particular an olfactory receptor of family 51 subfamily E member 2 (OR51E2), and
  (iii) a vomeronasal receptor, preferably vomeronasal 1, in particular vomeronasal 1 receptor 4 (VN1R4);
  (iv) a pheromone receptor; and
(b) an opsin, in particular opsin 3 (OPN3).

In a preferred embodiment, the patient is suffering from a neoplasia, an autoimmune disease, an infection and/or a graft-versus-host disease, in particular wherein said patient is suffering from a neoplasia, in particular wherein said neoplasia is cancer, particularly breast cancer.

In a preferred embodiment, the step of determining the amount of at least one sensory receptor at the surface of said cell (step (ii) of the method) comprises contacting the cell with at least one compound selectively binding to the at least one sensory receptor, preferably wherein said compound is labeled, in particular fluorescently labeled, labeled by a contrast agent, spin-labeled and/or radioactively labeled, in particular wherein said compound is an antibody or an sensory receptor-binding fragment thereof.

As used throughout the invention, the term "contacting the cell" may be understood in the broadest sense as adding a substance to a cell that it may potentially has an effect of the cell. Depending on the pharmacologic properties of the compound and depending on whether the compound is used in vivo or in vitro, appropriate means of contacting the cell will be chosen.

For applications in the patient in vivo, it will be understood that the compound may be administered locally or systemically. Compounds that have a good bioavailability and pharmacokinetics will preferably be added to the patient systemically (e.g., by injection, orally or nasally). Alternatively or additionally, it may also be administered topically or subcutaneously. In case of a pharmaceutical composition comprising an antibody and/or an siRNA, injection will typically be most preferred. Then, the compound may exemplarily be injected intravenously (i.v.), intraperitoneally (i.p.), intraarterially (i.a.), intramusculary (i.m.), subcutaneously (s.c.) and/or locally such as, e.g., directly into the diseased tissue such as a tumor. Alternatively, the compound may be taken up orally, e.g., as a powder, a tablet, a pill, a capsule, a chewable capsule, syrup, juice, gel, liquid or paste. Alternatively, the compound may be taken up nasally (intra nasal) (e.g., as spray or aerosol), percutaneously (e.g., as cream, spray or ointment and/or via a coated plaster) and/or by inhalation (e.g., inhalation of an aerosol or of a spray).

For applications in vitro, e.g., in a cell culture, it will be understood that the compound may be administered to the cells in one or a combination of numerous ways. When the compound is intended to act at the outer surface of cells, such as an antibody binding to an exterior side of a sensory receptor, the compound may just be added to the cells. In contrast, when the compound is intended to act in the cytoplasm of cells, such as, e.g., siRNA, another compound influencing expression or a compound influencing intracellular signal transduction, it has to enter the cells. Then, when the pharmacologic properties are beneficial, the compound may also just be added to the cell. In contrast, when the pharmacologic properties are less beneficial, the compound may, exemplarily, be administered by electroporation, by means of the employment of transfection agents (e.g., lipofectamine, polyethylene imine (PEI), positively charged fatty acids), by means of the employment of cell-penetrating peptides (CPPs) or protein transduction domains (PTDs) conjugated to or complexed with the compound, by means of micro- and/or nanobeads, by means of micelles, by means of liposomes and/or by means of polymersomes.

For the further terms used in in the context of this method, the definitions laid out above in the context of the therapeutic use of the compound of the present invention also apply. Before the readout, the cells may optionally be washed with buffer and/or medium.

In an alternative preferred embodiment, the step of determining the amount of at least one sensory receptor at the surface of said cell (step (ii) of the method) comprises contacting the cell with at least one antagonist of the at least one sensory receptor, in particular wherein said antagonist is a small interfering ribonucleic acid (siRNA) or a small hairpin RNA (shRNA), complementary to said sensory receptor, co-incubating the cell contacted with the at least one antagonist with at least one CTL, and subsequently determining the CTL activity.

A particularly preferred embodiment of this method using siRNA is defined in detail in the examples of the present invention.

Co-incubating, as used throughout the invention, means that the cells are cultured under conditions enabling maintaining their viability. For mammalian cells, typically a temperature of between about 30° C. to about 40° C., in particular a temperature of about 37° C. is suitable. Cells may preferably be incubated in medium comprising nutrients. For a short co-incubation, they may alternatively also be incubated in an appropriate buffer. In any case, the pH will typically be in an extensively neutral range, i.e. between about pH 6 and pH 8, in particular between about pH 7.0 and pH 7.5. Co-incubation time may preferably last long enough to allow the occurrence of a CTL response. Typically it may last between 30 min and few days, in particular in the range of few hours such as, 1 hour, 2, 3, 4, 5, 6, 7, 8, 9, 10, 11, 12, 13, 14, 15, 16, 17, 18, 19, 20, 21, 22, 23 or 24 hours, preferably in a range between about 4 hours and 24 hours, even more preferably in a range between about 12 hours and 20 hours.

Before the readout, the cells may optionally be washed with buffer and/or medium.

The CTL activity may be determined by any means known in the art.

In a preferred embodiment, the step of determining the amount of at least one sensory receptor at the surface of said cell (step (ii) of the method) comprises determining the CTL activity by one of the following:

(i) by determining the viability of the cell co-incubated with the at least one CTL and comparing the viability with that of a sample comprising a comparable cell and CTLs not treated by said antagonist, or (ii) by determining the excretion of polypeptides typical for CTL activity, such as one or more interferon(s) (IFN), one or more interleukin(s) (IL) and/or one or more tumor necrosis factor(s) (TNF), and comparing the results with that of a sample comprising a comparable cell and CTLs not treated by said antagonist.

Based on the same principle that sensory receptors suppress CTL response, the invention further relates to a method for identifying compounds according to the present invention. Herein, we chose CTL-induced tumor cell death as the preferred selection criterion for the screen.

Based thereon, the invention further relates to a further aspect referring to a method for identifying an agent influencing the response of cells to CTLs, said method comprising the steps:

(i) providing cells expressing at least one surface polypeptide preventing CTL response and further also expressing a polypeptide enabling bioluminescence, in particular luciferase, (ii) contacting cells of step (i) with at least one agent of interest, (iii) co-incubating cells obtained from step (ii) with CTLs and an agent crosslinking the antigen receptors of the CTLs with a cell-surface molecule of the cells of step (ii), (iv) recovering the viable cells obtained from step (iii), (v) determining the bioluminescence of the cytosol of the cells obtained from step (iv), and (vi) comparing the bioluminescence of the cells contacted with at least one agent and with a negative control of cells not contacted with an agent and/or with one or more other agent(s).

As used herein, the term "identifying an agent" may be understood in the broadest sense as the finding of an agent that is able to influence the response of cells to CTLs.

In the context of the present invention "agent" may be understood in the broadest sense as any compound as defined above, therefore as any molecule, salt or molecular complex or aggregate that selectively binds to a sensory receptor. Herein, the agent will preferably have the properties defined as preferred embodiments in the context of the compound above. Accordingly, most preferably, the agent is an siRNA, in particular an siRNA reducing the expression of a sensory receptor, or an antibody binding to a sensory receptor or a group of sensory receptors, in particular wherein said antibody is a monoclonal antibody. Herein, the terms siRNA and antibody may be understood in the broadest sense as defined above. The person skilled in the art will notice that an siRNA as well as a sensory receptor-blocking antibody are particularly preferred agents when the CTL response is intended to be strengthened, whereas a T cell-sensory receptor crosslinking antibody may be a particularly preferred agent when the CTL response is intended to be decreased.

When conducting this method for identifying an agent influencing the response of cells to CTLs, the artisan conducting said method may test a single agent of interest (candidate agent) to be tested or uses a variety of agents or even a library of different agents. In such library of different candidate agents, the artisan conducting said method may test molecules of a related molecular structure (e.g., an antibody library, an RNA library, a DNA library, a polypeptide library, a small molecule library etc.) or may test molecules of a different molecular structure. When such testing is conducted, single candidate agents may be tested or one or more composition(s) each comprising a combination of two or more candidate compounds may be tested. When using an siRNA library, preferably, siRNA targeting mRNA encoding for the expression activity of a polypeptide typically localized at the cell surface and/or involved in cell signaling are selected. Preferably, when using an siRNA library, a composition comprising more than one, more than two, more than three, more than four or even more than five different siRNA molecules are concomitantly used that target the expression activity of the same polypeptide (i.e., reduce expression of the same polypeptide).

Most preferably, the method for identifying agents is a screening method, in particular a high throughput screening, more preferably a high throughput siRNA screen, in particular a high throughput siRNA screen identifying novel immune modulatory molecules that suppress immune rejection, in particular of neoplasia such as cancer, most particular of breast cancer. Therefore, the method also relates to a high-throughput RNAi screen (e.g., siRNA screen) for detection of immune-checkpoint molecules that mediate tumor resistance to CTLs. In general, we therefore established an assay that is able to measure actual tumor cell lysis mediated by cytotoxic T cells in a high-throughput co-culture setting.

The cells used in this method may be any cells that can be involved in a CTL response, i.e., preferably cells of mammalian origin, in particular cells of human origin. The cells preferably have the features as defined above. Most preferably, the cells are involved in abnormal growth cells such as, e.g., neoplastic cells, in particular cancer cells. As defined above, the cells can be obtained from a patient directly, may be the progeny of such cells after several generations or may be cell culture cells.

In order to enable the conduction of the present method for identifying agents, the cells express at least one surface polypeptide preventing CTL response. In this context, the cell can express such polypeptide(s) naturally or have been transfected with a gene active in said cells that encodes for such polypeptide(s). Typically, the cell, in particular when it is a cancer cells, will naturally express at least one polypeptide preventing CTL response. However, it may optionally be beneficial to additionally transfect the cells in order to obtain larger amounts of the respective polypeptide(s) to increase the CTL response-preventing effect and, as a result, to improve the readout of the method. Further, in particular cases, it may be beneficial to transfect a cell naturally not expressing one or more particular polypeptide preventing CTL response(s) with an active gene encoding therefore, to have a highly defined readout with a defined composition of those CTL response-preventing polypeptide(s).

In order to enable the readout of the method according to the present invention, the cells further also express a polypeptide enabling bioluminescence, in particular luciferase. This enables the easy quantification of viable cells.

In a second step, the cells are contacted with at least one agent of interest (candidate compound). Depending on the pharmacologic properties, the method will be chosen. In this context, the definition for contacting the cells above also applies. The cells may optionally be washed with buffer and/or medium.

Then, in a further step, the cells are co-incubated with CTLs and a further agent crosslinking the antigen receptors of the CTLs with a cell-surface molecule of the cells, wherein the cell-surface molecule will typically be a polypeptide or a complex comprising at least one polypeptide. Exemplarily the further agent crosslinking may be an antibody, in particular a bi-specific antibody. Preferably, one of the binding specificities of such bi-specific antibody is directed to a polypeptide expressed at the surface of T cells, whereas the other is expressed at the surface of the other cells to be tested. In a particularly preferred embodiment, the polypeptide expressed at the surface of T cells is CD3. In another particularly preferred embodiment, the polypeptide expressed at cells to be tested is EpCAM. In a most preferred embodiment, the polypeptide expressed at the surface of T cells is CD3 and the polypeptide expressed at cells to be tested is EpCAM. This crosslinking enhances the CTL response to a level improving the readout of the effect of the candidate agent. Most typically, the cross-linking agent may be an antibody, in particular an antibody with at least two binding specificities: one against a T cell surface polypeptide, the other to a polypeptide present on and/or in (preferably on) the cell contacted with the candidate agent.

The next step of recovering the viable cells may be performed by any means known in the art. Exemplarily, when the cells are growing adherently, a (simple) washing step with buffer and/or medium may be used to wash away the unviable cells and to recover the viable cells on the solid carrier. Alternatively or additionally, the viable cells may be recovered by other means such as, e.g., fluorescence associated cell sorting (FACS).

Then, the bioluminescence of the cytosol of the cells is determined. This enables the evaluation of the amount of viable cells because only the viable cells express the bioluminescent polypeptide. Preferably, the cells are lysed by any means (e.g., by means of one or more detergent(s) (e.g., Triton-X-100), by means of mechanical homogenization (e.g., by a Potter or Downs homogenizer, by a French press, by scratching) and/or by means of sonication. Then, optionally, cytomembranes may be extensively removed by centrifugation. An appropriate bioluminescence precursor compound and the respective cofactors are added and the bioluminescence is detected. Alternatively, the bioluminescence may also be determined in the viable cells.

Finally, the bioluminescence of the cells contacted with at least one candidate agent is compared with a negative control of cells not contacted with an agent and/or with one or more other agent(s).

The difference in bioluminescence between these samples, extensively corresponds reciprocally to the difference in CTL response. Therefore, when the bioluminescence is two times lower in a sample obtained from cells incubated with a particular compound compared to the bioluminescence obtained from a control sample, the CTL response in the sample with the compound had been increased two-fold.

It will be understood that the present invention also relates to a kit comprising means for carrying out the method for identifying agents according to the present invention as well as optionally further comprising a user manual.

The person skilled in the art will notice that the method does not only allow the identification of agents but also, in turn, the present method also allows a rapid and comprehensive determination of immune-modulatory genes in many tumor types which, as an entity, represent the "immune modulatome" of cancer. These genes are preferably identified by using an siRNA library. When a particular siRNA or a combination of several siRNAs targeting mRNA encoding for the same polypeptide (candidate polypeptide) shows a positive effect in the method, this shows that the polypeptide suppressed in expression is a polypeptide preventing CTL response. Then this polypeptide may potentially serve as a molecular target structure in the sense of the present invention and may be targetable by a compound according to the present invention.

The surface polypeptide preventing CTL response may be any polypeptide having this property known in the art.

In a preferred embodiment, the surface polypeptide is a sensory receptor, more preferably wherein said sensory receptor is selected from the group consisting of
(a) an olfactory receptor, preferably selected from the group consisting of:
  (i) a taste receptor, in particular a taste receptor type 2 (TAS2R), in particular taste receptor type 2 member 3 (TAS2R3),
  (ii) an olfactory receptor of family 1, 2 or 51, in particular an olfactory receptor of family 1 subfamily F (OR1F), in particular an olfactory receptor of family 1 subfamily F member 1 (OR1F1), an olfactory receptor of family 2 subfamily J (OR2J), in particular an olfactory receptor of family 2 subfamily J member 2 (OR2J2), or an olfactory receptor of family 51 subfamily E (OR51E), in particular an olfactory receptor of family 51 subfamily E member 2 (OR51E2), and
  (iii) a vomeronasal receptor, preferably vomeronasal 1, in particular vomeronasal 1 receptor 4 (VN1R4);
  (iv) a pheromone receptor; and
(b) an opsin, in particular opsin 3 (OPN3).

For the terms used in in the context of this method, the definitions laid out above in the context of the therapeutic use of the compound of the present invention also apply.

In a preferred embodiment, the CTLs are pre-activated CD8+ T-cells, in particular CD8+ T cells pre-activated by T cell receptor (TCR) stimulation through a CD3 specific antibody and/or a CD28 specific antibody.

Such antibody specific for CD3 or CD28 may be a monoclonal or polyclonal antibody stimulating a T cell response. Preferably it is a monoclonal antibody.

Alternatively, the CTLs may also be antigen-specific T cell clones, such as survivin-specific T cells like those that have been shown in various validation studies. The nature and affinity of the antigen-specific T cell clones will then depend on the tumor cell type used. Melanoma antigen-specific T cell clones (e.g., MART-1, gp-100 specific T cell clones), for instance, may be used for detecting of immune modulators expressed on melanoma cells. Optionally, also tumor infiltrating lymphocytes (TILs) from patients may be used as CTLs.

In a preferred embodiment, the agent is an siRNA, in particular an siRNA complementary to the messenger ribonucleic acid (mRNA) encoding for a polypeptide typically localized at the cell surface and/or involved in cell signaling.

In this method, agents having a potential influence on the interaction between a sensory receptor and a T cell may be identified. Therefore, a further aspect of the present invention refers to an agent identified by a method according to the present invention.

A yet further aspect of the present invention relates to the agent identified by a method according to the present invention or genetic material encoding therefore for use in a method for treating or preventing a disease associated with a pathologic cellular CTL response, in particular a disease selected from the group consisting of neoplasia, in particular cancer, an autoimmune disease, an infection and graft-versus-host disease.

For the terms used in the context of this aspect of the present invention the definitions laid out above in the context of the therapeutic use of the compound of the present invention also apply. This also applies to the below preferred embodiments thereof.

In a preferred embodiment, the agent according to the present invention enhances an immune response to an activated CTL, in particular in a patient suffering from a neoplasia, in particular cancer, preferably wherein the local surface concentration and/or T cell-binding activity of the surface receptor that prevents CTL response is reduced.

The present invention also relates to a pharmaceutical composition and a kit comprising the agent according to the present invention as well as optionally further comprising (i) one or more pharmaceutically acceptable carrier(s) and/or (ii) a user manual.

In another preferred embodiment, the agent is selected from the group consisting of:
(i) an agent reducing the expression of a sensory receptor, in particular an siRNA complementary to mRNA encoding for said sensory receptor, and
(ii) an agent preventing the T cell-binding activity to said sensory receptor, in particular wherein said agent is an antibody or a sensory receptor-binding fragment.

In an alternative preferred embodiment, the agent according to the present invention suppresses an immune response to an activated CTL, in particular in a patient suffering from an autoimmune diseases and/or graft-versus-host disease, preferably wherein the amount and/or T cell-binding activity of the surface receptor that prevents CTL response is enhanced.

In a preferred embodiment, the agent is selected from the group consisting of:
(i) genetic material encoding for a sensory receptor,
(ii) an agent enhancing the expression of said sensory receptor, and
(iii) an agent cross-linking a surface polypeptide preventing CTL with a T cell, in particular a cross-linking antibody or antibody fragment.

In a preferred embodiment, the agent is used in combination with one or more further immunomodulatory agent(s).

The present invention further refers to a method of preventing a disease associated with a pathologic cellular cytotoxic T cell in a subject by administering to said subject a sufficient amount of a compound selectively binding to a sensory receptor or selectively altering the expression of a sensory receptor.

The present invention further refers to a method of diagnosing cellular resistance against CTL response in a subject by administering to said subject a sufficient amount means for detecting a sensory receptor.

The following figures and example are intended to illustrate the invention but not to limit the scope of protection conferred by the claims.

BRIEF DESCRIPTION OF SEVERAL VIEWS OF THE DRAWINGS

FIG. 10 shows the viability of luciferase transfected MCF7 breast tumor cells transfected with different gene specific siRNAs as measured by luciferase activity (RLU) after co-culture with tumor antigen specific cytotoxic T cells (survivin specific CTL clone) (A) or without T cell co-culture (B). Reduced luciferase activity indicates tumor cell death. Unspecific scrambled siRNA (sc RNA) was used as negative control; luciferase specific siRNA (fluc) as positive control.

EXAMPLES

Example 1

Materials and Methods

Cell Culture and Reagents

Figure 1A:
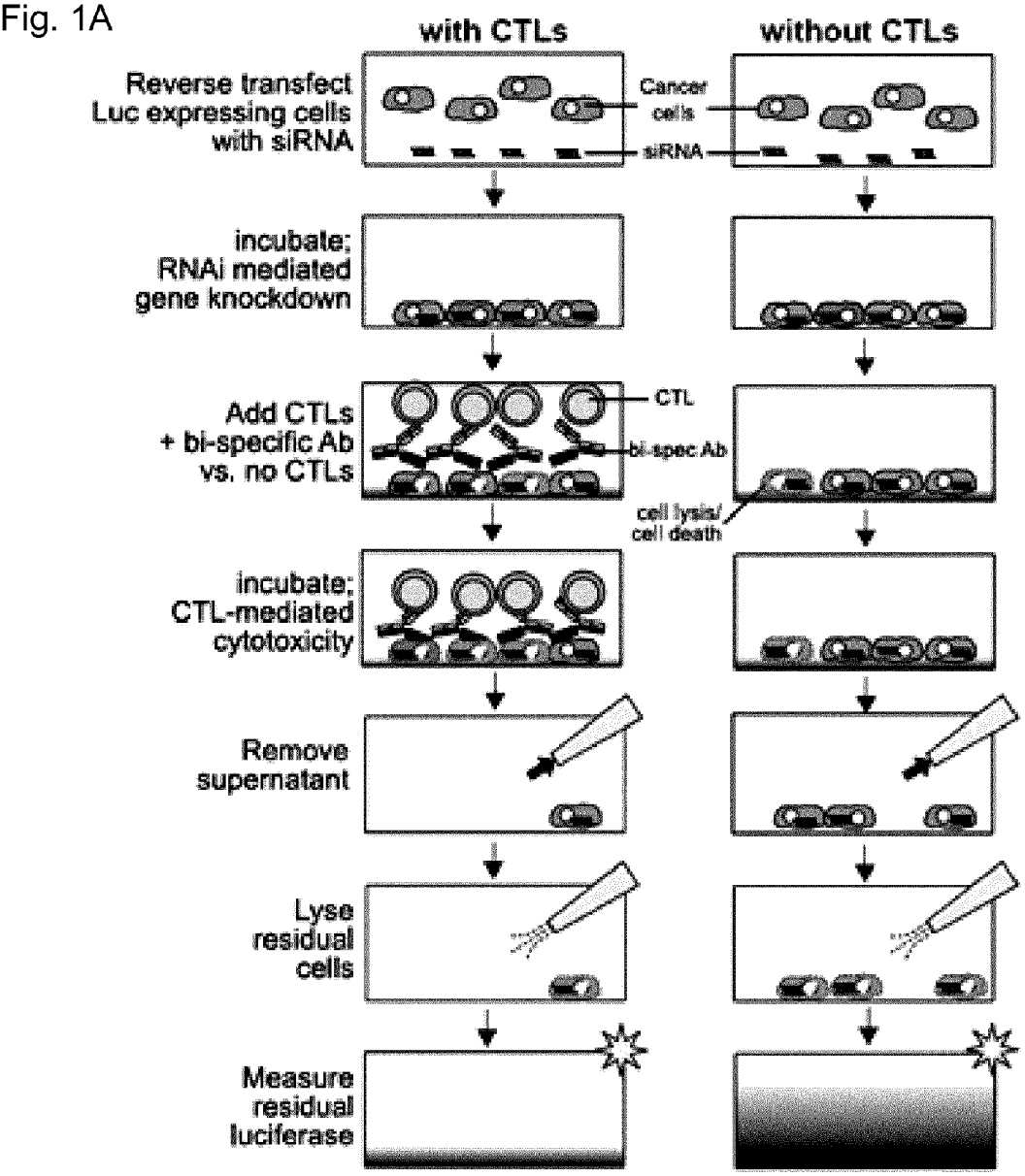
FIG. 1 shows Luc-CTL assay design used for identification of immune-checkpoint molecules. (A) RNAi is performed with luciferase expressing cells that are challenged with or without CTLs and bi-specific antibody (bsAb). Before readout, cell supernatant is removed and the remaining intact cells are lysed to measure the residual cell-associated luciferase. To identify immune checkpoint regulators, the difference between normalized luciferase measurements for conditions with CTLs and without CTLs is calculated. SiRNA enhancing CTL cytotoxicity will only reduce normalized luciferase levels under conditions with CTLs, hence the difference between luciferase measurements will be >0. (B) Luc-CTL assay performed at different T cell to MCF7 cell ratio with PBMC-derived CD8+ T cells and anti-CD3×anti-EpCAM bi-specific antibody (○). Anti-CD3×anti-CD19 bi-specific Ab (■) was used as a specificity control since CD19 is a B-lymphocyte-specific antigen and therefore this bsAb fails to crosslink tumor to T cells. Lower luciferase intensity indicates higher lysis. (C) Luc-CTL assay was performed with MCF7 cells transfected with control or PD-L1-specific siRNAs and co-cultured with or without CTLs and bsAb. For each condition, the luciferase activity of PD-L1-siRNA treated cells was normalized to that of the control treatment and is shown here; n=8. (D) Comparison between the Luc-CTL assay (■) and the classical chromium release assay (○) with MCF7 as target cells and survivin-specific T cells as effector cells at varying E:T ratios. Error bars denote+/−SEM.
Figure 1A:
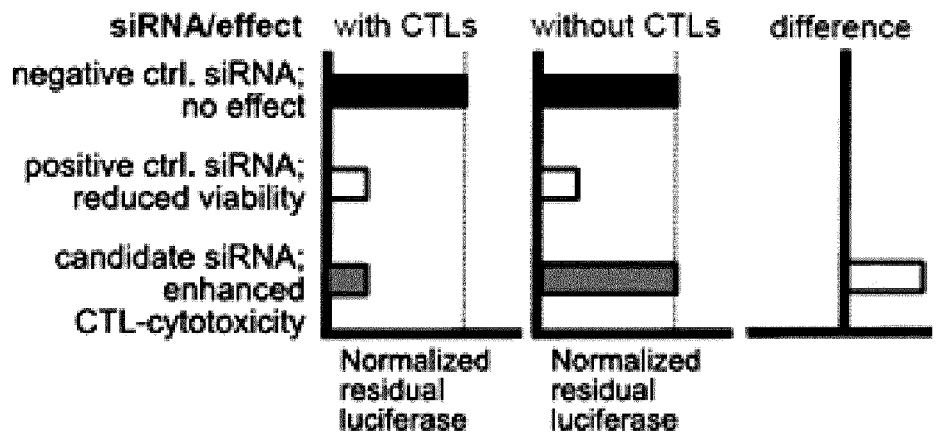

MCF7, MDA-MB-231 and KS breast cancer cells were acquired from the American Type Cell Culture (Wesel, Germany) and cultured in DMEM (Sigma, Germany) containing 10% FCS at 5% CO2 and 37° C. The candidate polypeptide-high MCF7-C6 breast cancer cell line was generated by FACS sorting and expansion of positive MCF-7 cells using specific mAbs (Axxora, Lörrach, Germany). MCF7-Luc cell line was generated by electroporating the parental cell line with pEGFP-Luc plasmid (generously gifted by Dr. Rudolph Hasse, LMU, Munich) and culturing the FACS-sorted GFP+ clones in media containing 550 µg/ml of selection antibiotic G418 (Gibco, UK).

For the RNAi screen, CD8+ T cells were isolated from the PBMC of healthy donors after ficoll separation using CD8 Flow Comp kit as recommended by the manufacturer (Dynal, Invitrogen; Karlsruhe, Germany). Purified T cells were cultured for 3 days in X-vivo media (Lonza, Belgium) in the presence of 100 U/mL interleukin 2 (IL-2) and anti-CD3/CD28 activation beads as detailed in the manufacturer's protocol (Dynal, Invitrogen). Polyclonal T cells were cross-linked to the tumor using anti-CD3×anti-EpCAM bi-specific antibody which was kindly provided by Dr. Gerhard Moldenhauer (DKFZ, Heidelberg, Germany). CTL clones specific for HLA-A0201 restricted epitopes of breast tumor associated antigens survivin95-104 (clone SK-1) and HER2369-377 (clone KU-1) were generated from peripheral blood T cells of healthy donors as described before (Conrad et al., 2008, and Bracketz et al., 2011). The TAP-deficient cell line T2 expressing HLA-A0201 was used for loading HLA-0201-restricted peptides in some cases.

RNAi Screen

A sub-library of the genome-wide siRNA library siGENOME (Dharmacon, Thermo) targeting mostly GPCRs was used for RNAi screening. The library contained 516 siRNA pools, consisting of four synthetic siRNA duplexes each and was prepared as previously described (Gilbert et al., 2011). Positive and negative siRNA controls with known phenotypes, e.g. non-targeting siRNAs (Ambion), siRNA targeting genes that affect cell viability (e.g. UBC, PLK-1) or known to affect CTL cytotoxicity (e.g. PD-L1), as well as additional siRNAs targeting genes potentially involved in immune checkpoint regulation e.g. like RCAS1 (Han et al., 2007) and Gal-3 (Peng et al., 2008) (all from Dharmacon) were distributed into empty wells prior to screening.

Beside others, the following siRNA sequences depicted in Table A are used herein:

TABLE A siRNA sequences

| TAS2R3_siRNA ID | siRNA sequence | SEQ ID NO: |
|---|---|---|
| s1 | GUACCUGCCUCCCUUAAUU | SEQ ID NO: 1 |
| s2 | GGUAGCAGCUGGUUCAAGA | SEQ ID NO: 2 |
| s3 | CCGCAUCUCUGAUCAAUGA | SEQ ID NO: 3 |
| s4 | GCAGACAUUUGUAGUGAUG | SEQ ID NO: 4 |
| OR51E2_siRNA ID | | |
| s1 | GUACACCGCUUUGGAAACA | SEQ ID NO: 5 |
| s2 | GAAACUGCAUCGUGGUCUU | SEQ ID NO: 6 |
| s3 | CAUGCCACCUUUGUGCUUA | SEQ ID NO: 7 |
| s4 | CCAAUGUGGUAUAUGGUCU | SEQ ID NO: 8 |
| PD-L1 | Mix of 4 siRNAs: | |
| | UGAAAGGACUCACUUGGUA | SEQ ID NO: 9 |
| | CAUAGUAGCUACAGACAGA | SEQ ID NO: 10 |
| | AGACCUGGCUGCACUAAUU | SEQ ID NO: 11 |
| | GGACCUAUAUGUGGUAGAG | SEQ ID NO: 12 |
| RCAS1 | Mix of 4 siRNAs: | |
| | GAAACUAGCAGACAGAGAA | SEQ ID NO: 13 |
| | GGACGGAAAUUAAGUGGAG | SEQ ID NO: 14 |
| | GGACAUGACACCAACUAUU | SEQ ID NO: 15 |
| | GAAGCACAACGGCUAAUGA | SEQ ID NO: 16 |

In order to comprehensively identify immune checkpoint regulators in an unbiased manner, we harnessed a previously described approach to measure tumor-specific T-cell cytotoxicity which is based on quantifying residual cell-associated luciferase expression following exposure of Luc-expressing cancer cells with CTLs (Brown et al., 2005). We adapted and extended aforementioned approach for high-throughput RNAi screening purposes and termed it 'Luc-CTL' assay. Briefly, the screening experiment was set up as follows: In total, three RNAi screens were performed in duplicate and reverse transfection of cells with siRNA pools was performed by delivering 15 μl of RPMI (Invitrogen) containing 0.05 μl of RNAiMAX (Invitrogen). After 30 min of incubation at room temperature, 3000 MCF7 cells (screen 1: MCF7 stably expressing luciferase, screen 2 and 3: wild-type MCF7 cells) in 30 μl of DMEM medium (Invitrogen) supplemented with 10% FBS (Invitrogen) were added to the siRNA transfection mix. Plates were then incubated at 37° C., 5% $CO_2$. 24 h later, cells were either transiently transfected with a luciferase expression plasmid (screen 2) using TransIT-LT1 transfection reagent (Mirius Bio LLC, Madison, USA) according to the manufacturer's instructions or not (screen 1 and screen 3). 72 h post siRNA transfection cancer cells were either challenged with CTLs and anti-CD3×anti-EpCAM bi-specific antibody (screen 1 and screen 2; condition with addition of CTLs) or not (screen 1 and screen 2; condition without addition of CTLs and screen 3). For screen 1, one batch of CTLs derived from one single donor was employed. For screen 2, two batches of CTLs derived from 2 different donors were employed. 18 h later, supernatant was removed, cells were lysed and luciferase measurements (screen 1 and 2) or viability measurements (screen 3) using CellTiter-Glo (Promega) were performed as previously described (Gilbert et al., 2011, and Muller et al., 2005). All dispensing steps were performed with a Multidrop Combi dispensing system (Thermo).

Data Analysis

Plate reader data from RNAi screens were statistically analyzed using the cellHTS2 package in R/Bioconductor (Boutros et al., 2006). Briefly, plate-based normalization was performed and a robust z-score method embedded in cellHTS2 was employed. In order to compensate for obvious row effects within plates, b-score normalization was employed where necessary. For screen 1 and screen 2, scores from both conditions, i.e. addition of CTLs and without addition of CTLs, were further quantile normalized against each other using the aroma.light package in R. Differential scores were calculated by subtracting quantile normalized scores without addition of CTLs from scores derived with addition of CTLs. In order to robustly identify genes that positively modulate CTL mediated cytotoxicity and to avoid biases potentially introduced by employing CTLs from different donors and employing genetically engineered as well as unmodified MCF7 cells, the 150 top-ranking genes as evaluated by the differential score were extracted for the independent screens 1 and 2 and the overlap between candidate lists was determined. Filtering of candidate lists to compensate for viability effects as well as potential effects on luciferase expression elucidated by siRNAs was performed by excluding the bottom 10 and top 25 genes based on scores as derived from residual luciferase measurements without addition of CTLs from the overlapping candidate list. Finally, genes scoring in a CellTiterGlo-based viability screen (screen 3) were filtered out from the candidate list (score <−1.5 and >1.5). Thereby, siRNAs generally affecting cell viability, as determined by intracellular ATP levels, could be excluded.

Network Analysis

The interaction network for the identified candidate genes was generated using the Ingenuity Pathways Analysis (IPA) web application (www.ingenuity.com). Gene symbol identifiers were uploaded to IPA and direct or indirect interactions were queried between these gene objects with the following parameters: 'species=Human' and 'confidence=Experimentally Observed'. Genes or gene products are represented as nodes, and the biological relationship between two nodes is represented as an edge (line). All edges are supported by at least 1 reference from the literature or from canonical information stored in the Ingenuity Pathways Knowledge Base.

Western Blot and RT-PCR

Whole cell protein extracts for western blot analysis were prepared as described before. Antibodies used for western blot were anti-candidate polypeptide human antibodies, anti-human PD-L1 (R&D systems), anti-human beta-actin (Abcam). Total RNA was extracted from cell pellets using the RNeasy Micro kit (Qiagen, Hilden, Germany) and reverse transcribed using the QuantiTect reverse transcription kit (Qiagen) as instructed by the manufacturer. Primer sequences for PCR run:

```
PD-L1 Forward:
                            (SEQ ID NO: 17)
5'-GTACCTTGGCTTTGCCACAT-3', PD-L1 Reverse:
                            (SEQ ID NO: 18)
5'-CCAACACCACAAGGAGGAGT-3', GAPDH Forward:
                            (SEQ ID NO: 19)
5'-GAGTCAACGGATTTGGTCGT-3', GAPDH Reverse:
                            (SEQ ID NO: 20)
5'-TTGATTTTGGAGGGATCTCG-3'.
```

Cytotoxicity Assay

For the chromium-release cytotoxicity assay, tumor cells were first transfected with the described siRNAs in 25 m2 culture flasks using RNAiMax transfection reagent, as described above. In some experiments, for overexpression of a candidate polypeptide, MCF7 cells were either transfected with pCMV6-AC-His-candidate polypeptide encoding vector (OriGene, Rockville, US) or pCMV6-AC-His control vector using TransIT-LT1 transfection reagent (Mirus, Madison, USA), as per manufacturer's protocol. 72 hours later, the siRNA or plasmid transfected cells were harvested, washed and labeled with 200 $^{51}$Cr/10$^6$ target cells (Perkins-Elmer, Germany) for 45 min at 37° C. For antibody blockade of another candidate polypeptide, 1×10$^6$ MCF7-C6 cells were first incubated with 30 ug/ml of blocking antibody for 30 minutes on ice and then washed and labeled with chromium. After labeling, the cells were carefully washed thrice to remove cell-free chromium and 3000 target cells/well were co-cultured with T cells in 96 well plates at a T cell to target cell ratio of 1:1 to 100:1 for 4 hours at 37° C. After 4 hours, the plates were spun down and the supernatant was harvested for measuring the radioactivity released by dead cells using the Gamma counter (Cobra counter Packard, Perkin Elmer, Rodgau, Germany). We also used polyclonal CD8 T cells from healthy donors as effector cells for induction of breast cancer cell lysis. To this end, CD8+ T cells were isolated from PBMC of healthy donors and activated using anti-CD3/anti-CD28 activation beads as described above. Subsequently, these activated CD8 T cells were then co-cultured with 3000 radioactively labeled target cells/well at a T cell to target cell ratio of 1:1-100:1 for 4 hours and in the presence of 5 µg/ml of anti CD3×anti EpCAM bispecific antibody or anti-CD3×anti-CD19 control bi-specific antibody. As a control for spontaneous release, the labeled cells were co-incubated with media alone; for maximum release, the cells were incubated with 10% Triton X-100 instead of T cells. % specific lysis was then calculated by the formula given below:

% specific lysis=(Experimental release−Spontaneous release)/(Maximum release−Spontaneous release)×100

ELISpot Assays

IFN-γ, perforin and granzyme B secretion from T lymphocytes were determined using the ELISpot assays as detailed by the manufacturer (Mabtech, Nacka Strand, Sweden). Briefly, the immune-suppressive candidate genes were inhibited in the tumor cell lines using specific siRNAs, along with control knockdown. 48 hours post siRNA transfection, the knocked down cells were harvested, washed and co-cultured with survivin-specific T cells in ELISpot wells at a ratio of 5:1 effector to target ratio for 24 hours. Additionally, in some cases, the cells were co-cultured in the presence of varying concentrations of candidate polypeptide blocking antibody (Axxora). IFN-γ, perforin or granzyme B spots were measured using enzyme-linked immunospot (ELISPOT) software (Zeiss, Jena, Germany or CTL Europe, Bonn, Germany). Statistical comparison was performed from three test wells per group. In some experiments, T2 cells pulsed with 20 µg/ml HLA-A2-restricted peptides were used instead of tumor cell lines as positive controls of immune response.

Cytokine Measurements

Cytokine levels in the cell culture supernatant from tumor and T cell co-incubation experiments were determined using the Bio-plex cytokine assay that employs antibody-coupled fluorescent beads for analyte quantification using a two-laser flow cytometer. Briefly, the MCF7 cells were transfected with candidate polypeptide-specific or control siRNA for 48 hours and then harvested and co-cultured with 10$^4$ survivin-specific T cells at 1:5 ratio in 96-well plate for additional 24 hours at 37° C. Three test wells per group were included in this study. After incubation, the plates were spun down and 100 µl of the culture supernatant was collected from each test well and centrifuged at 1000×g for 15 min at 4° C. The clear supernatant was collected and used directly for cytokine measurement using the Bio-Plex Pro Assay kit as described by the manufacturer (Biorad, Germany). Data was analyzed using the Bio-Plex Manager software version 6.0.

Phosphoprotein Analysis

MCF7 cells were transfected with either control or specific siRNAs as described above. After 72 hours, the cells were harvested and 8×10$^4$ cells in 100 µl of cytokine free X-vivo 20 medium were plated per well of a 96-well plate. To this 2×10$^6$ survivin-specific T cells, suspended in 100 µl of X-vivo medium, were added. For polypeptide blockade, instead of siRNA transfection, the KS cells were either untreated or pretreated with 30 m/ml anti-candidate polypeptide mAb for 30 min on ice followed by careful washing. The tumor and T cells were co-cultured for 5 min for T cell receptor complex analysis and 2 hours for phospho-STAT analysis. Post co-incubation, the cells were harvested, washed and lysed. The total protein concentration was measured using BSA Protein Assay Kit (Thermo scientific, Rockford, U.S.) and this was normalized across all samples before phosphoprotein detection using the 7-plex T cell receptor signaling phosphoprotein kit or phospho-STAT 5-plex kit (Millipore, Billerica, U.S.), as instructed by the manufacturer. Measurements were performed using Luminex100 Bio-Plex System (Luminex, Austin, U.S.) and all the data were analyzed using Bio-Rad Bio-Plex Manager software version 4.1.1 (BioRad Life Science Research, Hercules, U.S.).

Adoptive T Cell Transfer Experiments 6-8 weeks old female NOD/SCID mice (strain NOD/NCrCrl-Prkdcscid) were obtained from Charles River (Sulzfeld, Germany) and kept under SPF conditions. Mice were engrafted with $2 \times 10^6$ KS breast cancer cells in 50 µL of matrigel basement membrane matrix (BD Biosciences) s.c. on the right flank. When tumors reached a diameter of 6-8 mm (app. 18 days after tumor implantation), mice were transferred two times intravenously with $5 \times 10^6$ survivin specific CTL (clone: SK-1)/100 µl PBS. In addition, mice received twice a week 4 to 7 i.p. injections with 50 µg-200 µg of anti-candidate polypeptide or isotype mAb. Tumor growth was assessed twice a week according to the formula volume=(length×width$^2$×π/6).

Statistical Evaluation

Differences between test groups and control groups were analyzed using two-sided student t-test. In all statistical tests, an effect was considered as statistically significant if the P-value ≤0.05.

Design of a High-Throughput RNAi Screen

In order to identify tumor-associated genes that inhibit cell killing by cytotoxic T lymphocytes (CTL), we adapted a luciferase-based readout assay, henceforth referred to as Luc-CTL assay (FIG. 1A). For this assay, we established a luciferase-expressing MCF7 breast cancer cell line (MCF7luc) by stable transfection and also performed transient luciferase transfection of MCF7 cells which allows a rapid screening of various tumor cell lines in the future.

Figure 1B:
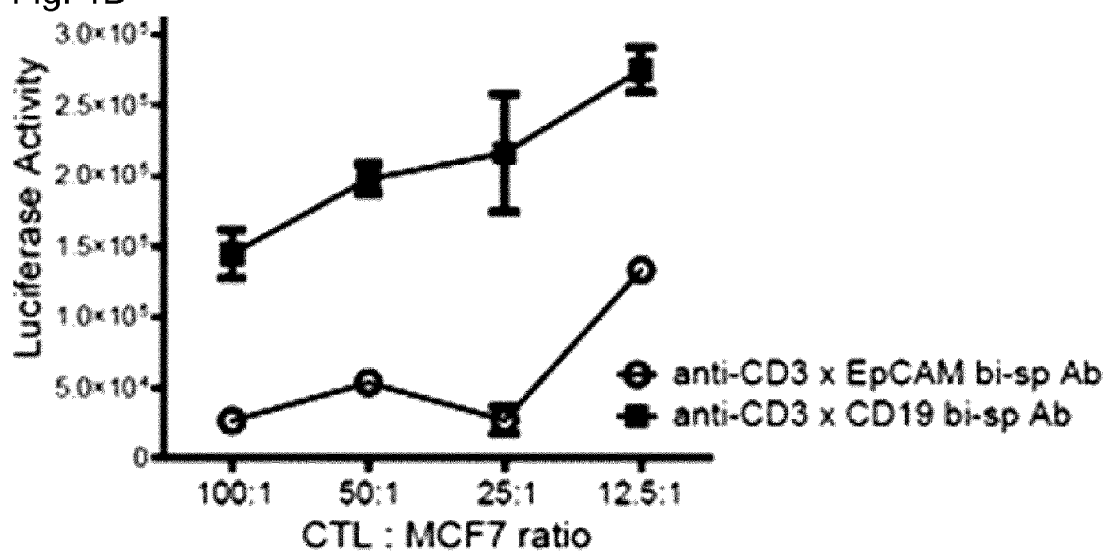
Figure 1C:
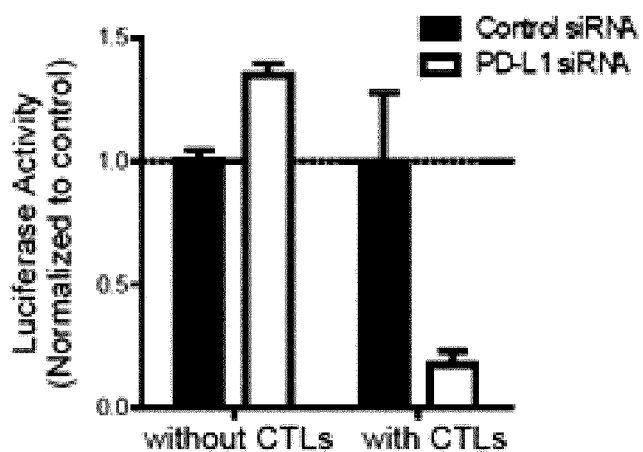
Figure 1D:
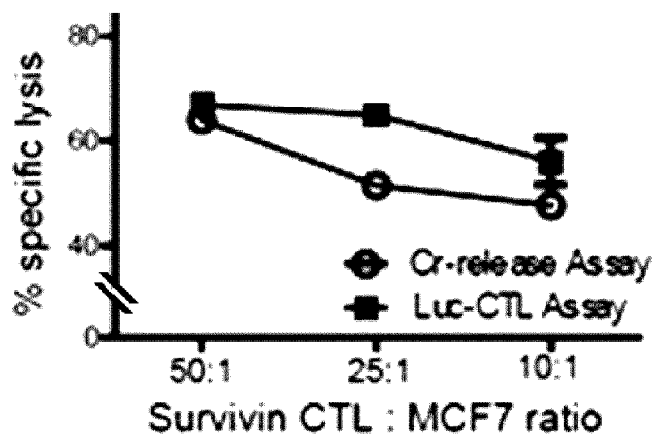

To induce tumor cell lysis by CTL, we cross-linked the antigen receptors of purified and pre-activated CD8+ cytotoxic T cells from healthy donors to the cell surface of tumor cells using bi-specific antibodies recognizing with one arm the T cell receptor associated molecule CD3 and with the other arm the cell surface molecule EpCAM which is highly expressed on most epithelial tumors but not on leukocytes (Strauss et al., 1999). This efficiently induced T cell activation and tumor lysis in a dose dependent manner as determined by the strongly reduced luciferase activity of the remaining tumor cell population after co-culture with increasing amounts of T cells (FIG. 1B). To identify genes that protected tumor cells from CTL induced destruction MCF7luc cells were reversely transfected in 384-well plates (3000 tumor cells/well) with pooled siRNAs, containing 4 different siRNA sequences per target, and co-cultured with $3 \times 10^4$ pre-activated donor-derived CD8+ T cells for 18 h. In order to exclude genes whose knockdown in itself impacts on cell viability, the Luc-CTL assay included a viability control per gene knockdown, to which no CTLs were added. We calculated the difference in luciferase activity between test wells (containing CTLs) and control wells (without CTLs) and selected only those genes for further analysis that revealed a positive value (FIG. 1A). To explore the validity of the Luc-CTL assay we performed proof-of-concept validation experiments with PD-L1, which mediates strong immune suppression in breast cancer (Dong et al., 2002). PD-L1 knockdown did not influence MCF7luc viability by itself, but strongly increased CTL induced tumor cell death (FIG. 1C). We therefore used PD-L1 as a positive control in our subsequent high-throughput screens. Importantly, the extent of tumor cell killing detected by the Luc-CTL assay was comparable to that obtained with a common test of T cell mediated cytotoxicity, the $^{51}$chromium-release assay (Brunner et al., 1968) (FIG. 1D).

To apply the Luc-CTL assay to a high-throughput screening approach we focused on a library of 520 genes coding for transmembrane and cell surface-associated proteins because such molecules are suitable targets for therapeutic function-blocking antibodies and are therefore of particular clinical relevance.

Figure 2A:
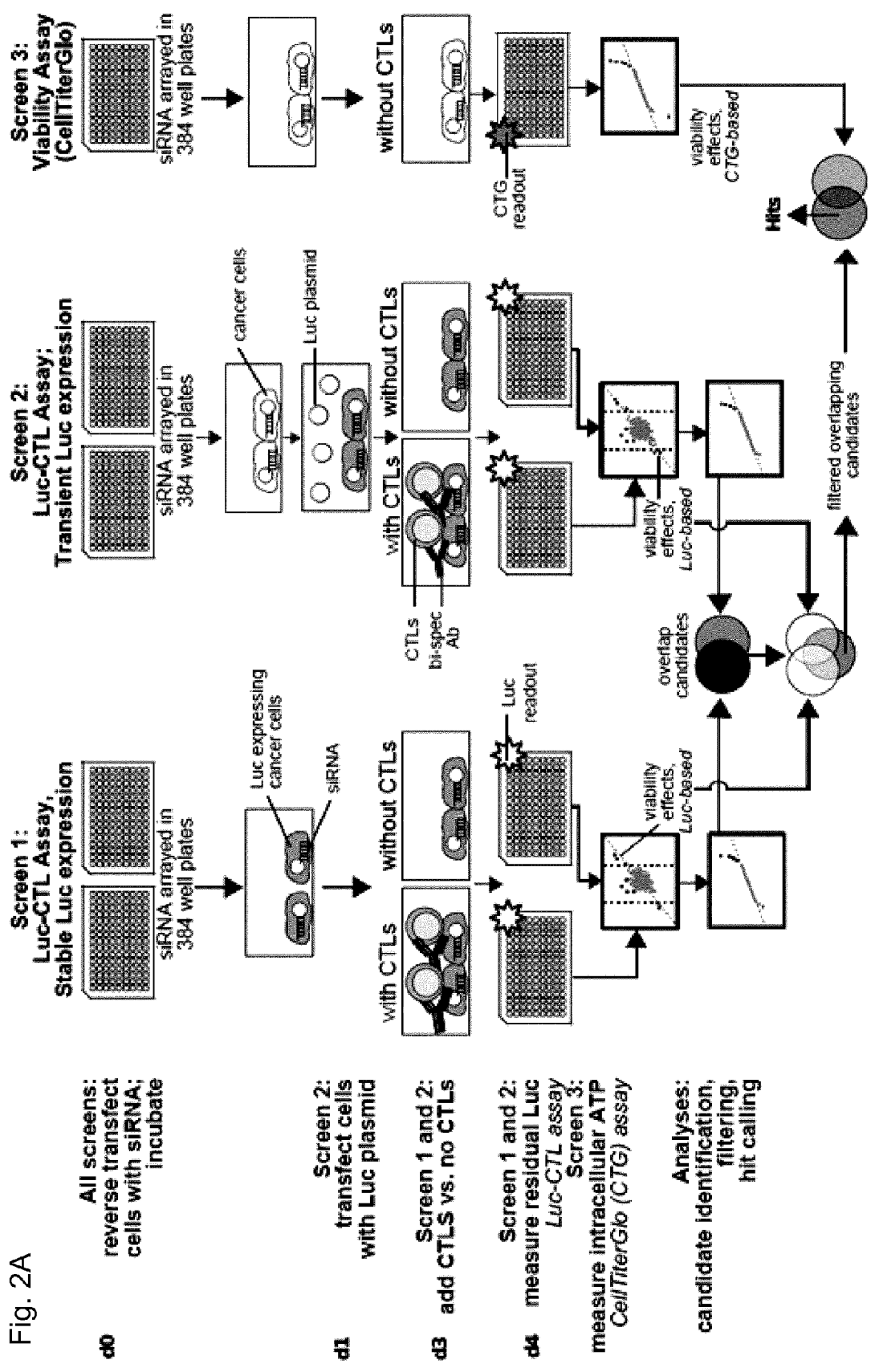
FIG. 2 shows the layout and analysis of the RNAi screen used to identify immune-modulatory tumor genes. (A) Workflow and experimental layout of the RNAi screen which was performed twice, each time in duplicates, along with an additional CTG-based viability screen to filter out lethal genes from the final hit list. Hits were analyzed after data normalization using the cellHTS2 package. (B) Graphical summary of gene function related to modification of T cell mediated tumor lysis and cell viability. Positive score=reduced cancer cell viability, negative score=increased viability. X axis: Influence on cell viability without addition of T cells. Y axis: Influence on cell viability with addition of T cells. Appropriate immune-suppressive (PD-L1, RCAS-1, GAL-3) and lethality (UBC, PLK-1) controls and few hits (two exemplary candidate compounds) are highlighted herein. (C, D) Differential score between the viability set and toxicity set for both screen-1 (C) and screen-2 (D) are plotted against the genes tested in this study. PD-L1 sample wells were contaminated in screen-2 and therefore excluded from the analysis. (E) Top 150 hits from both the screens were analyzed for overlapping hits and high scorers from the viability set were filtered out from these hits for both the screens. Additional genes were filtered out based on CTG assay, resulting in a consensus pool of 42 top genes that negatively regulate CTL activity against MCF7 cells.

The candidate identification procedure is outlined in FIG. 2A. We conducted the screen in parallel with MCF7luc cells and transiently luciferase transfected MCF7 cells using as CTL purified CD8+ T cells from healthy donors that had been pre-activated by polyclonal TCR stimulation through CD3 and CD28 specific antibodies (mAbs). Each screen was conducted in a set of 4 replicates, two of which were co-cultured with CTLs and bi-specific antibody (toxicity set) and the other two were incubated without CTLs and bi-specific antibodies (viability set). We first identified in both screens those 150 genes whose knockdown revealed the highest cytotoxicity in the Luc-CTL assay. We selected from these groups those genes that were simultaneously detected in both screens. Based on their viability set scores we then excluded those genes that impacted cell viability. Finally, we employed data from an additional screen (based on CTG assay) in which the impact of gene knockdown on the viability of MCF7 cells was determined independent of luciferase activity by measuring intracellular ATP levels (FIG. 3). Genes that reduced cell viability as measured by this assay were also excluded.

Figure 2B:
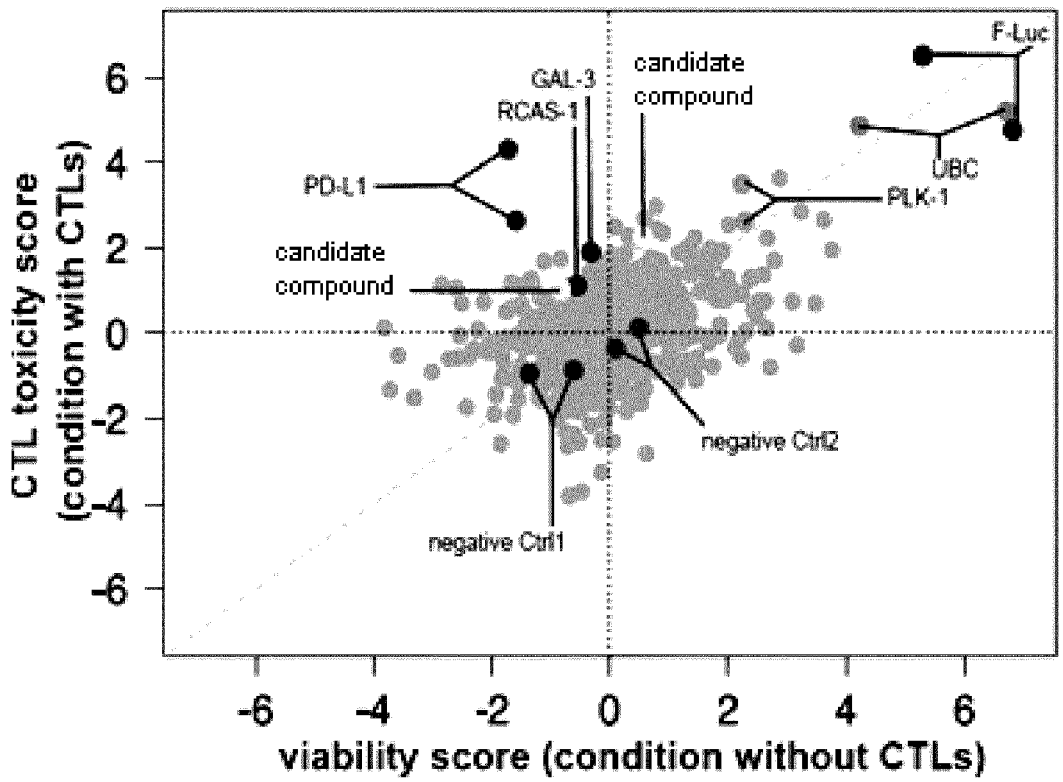
Figure 3A:
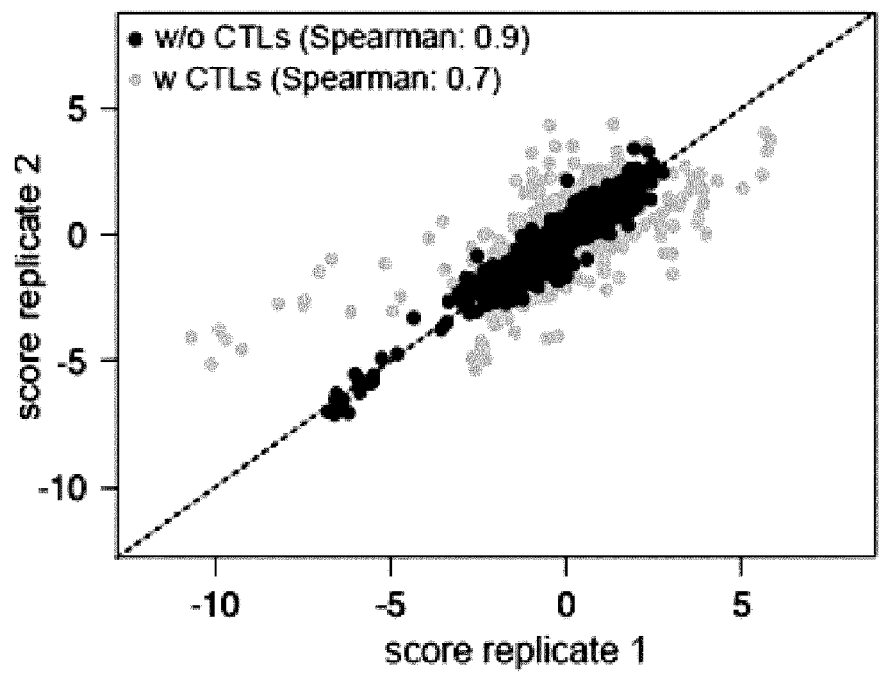
FIG. 3 shows (A) the performance of replicates of screen-1 for toxicity set (with T cells) and viability set (without T cells) as determined by the Spearman rank correlation test. (B) CTG assay for determining lethal genes that directly affect MCF7 cell viability upon knockdown.

An overview of the data derived from the first screen is given in FIG. 2B. The reproducibility between the replicates within the individual screens was high for both the toxicity set (Spearman rank correlation coefficient: 0.7) and the viability set (Spearman rank correlation coefficient: 0.9) (FIG. 3A). SiRNA against the luciferase gene (FLuc) expectedly resulted in abrogation of the luciferase signal under both conditions and served as an internal control for the luciferase-based readout. As anticipated, control siRNAs targeting genes indispensable for cell survival (UBC and PLK-1) induced prominent cell killing under both conditions (without and with CTLs; x-axis and y-axis, respectively) (FIG. 2B). In contrast, scrambled negative control siRNAs did not affect the luciferase signal under either condition. Thus, UBC and PLK-1 on one hand and negative control siRNA1 and siRNA2 on the other hand are suitable to define the range of cytotoxicity among which candidate genes can be ranked according to their impact on CTL-mediated tumor cell lysis. The knockdown of three genes with reported function as immune regulatory molecules on tumor cells, namely PD-L1, galectin-3 and RCAS-1 strongly reduced luciferase activity only in the cytotoxicity setup, whereby PD-L1 showed the highest and RCAS-1 the relative lowest impact on T cell mediated tumor cell lysis. These therefore served as immune modulatory reference genes throughout the screens (Blank et al., 2004, Han et al., 2007, and Peng et al., 2008).

Figure 2C:
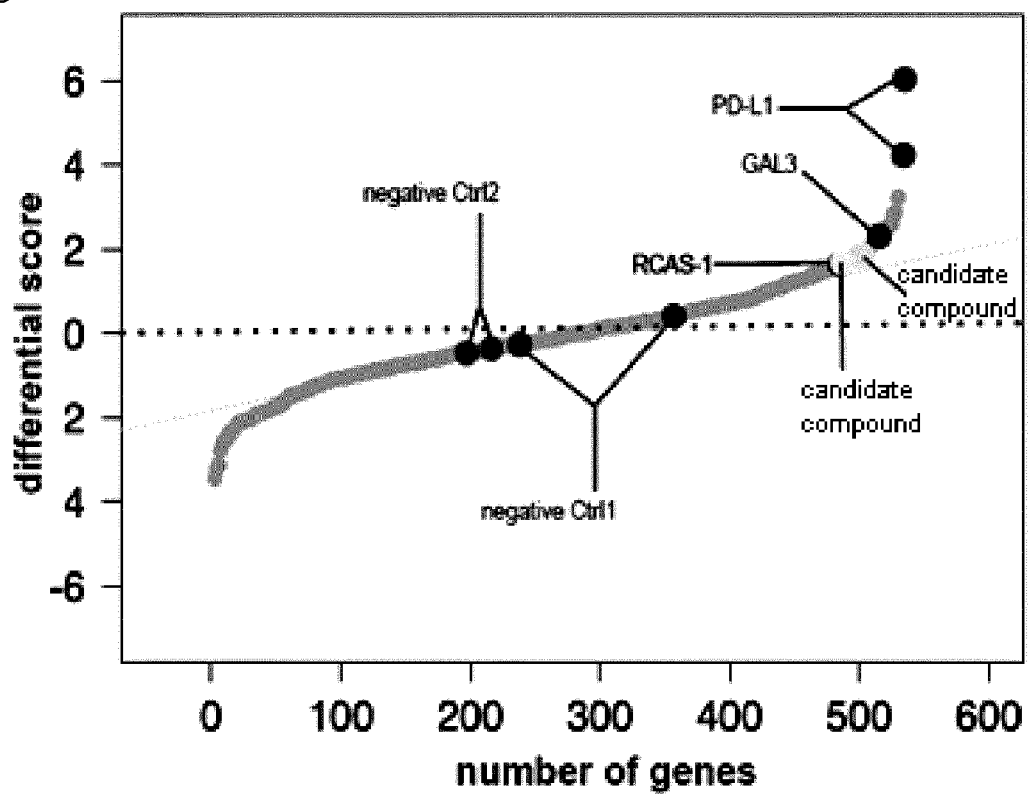
Figure 2D:
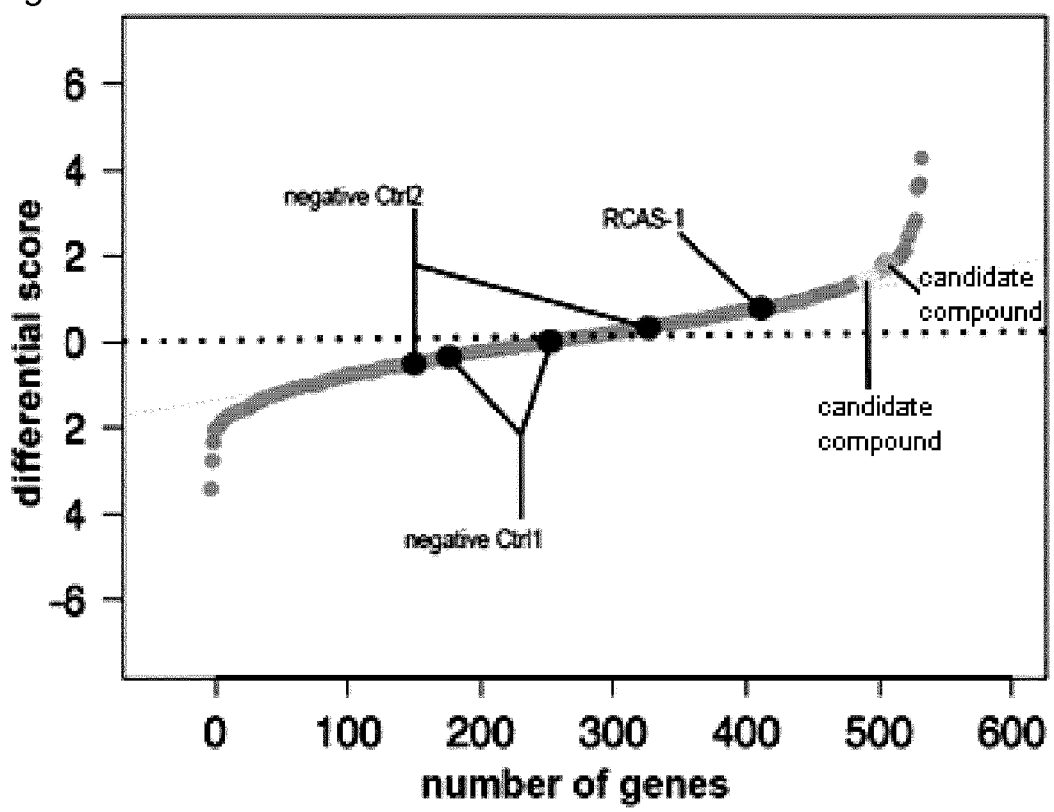
Figure 2E:
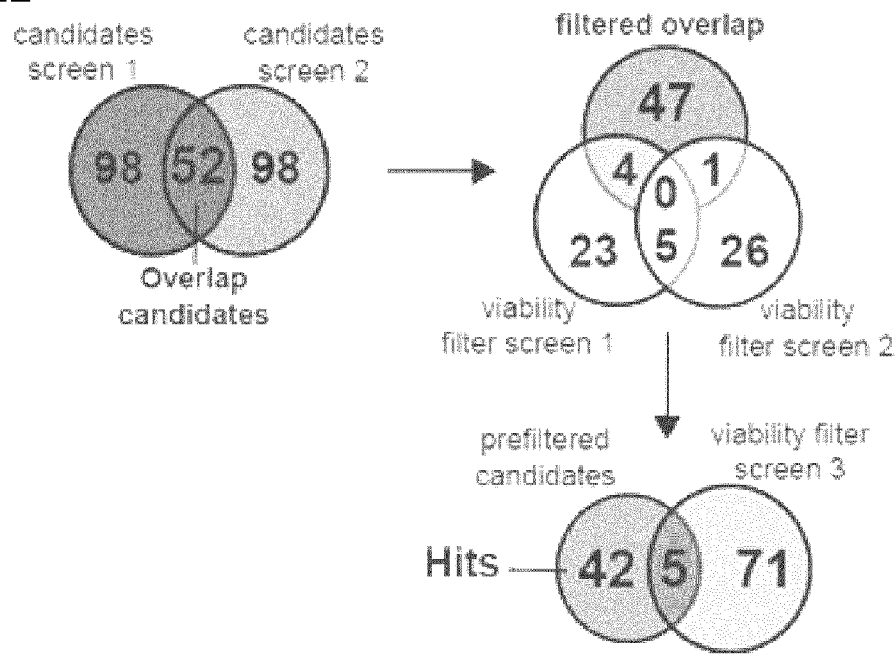
Figure 3B:
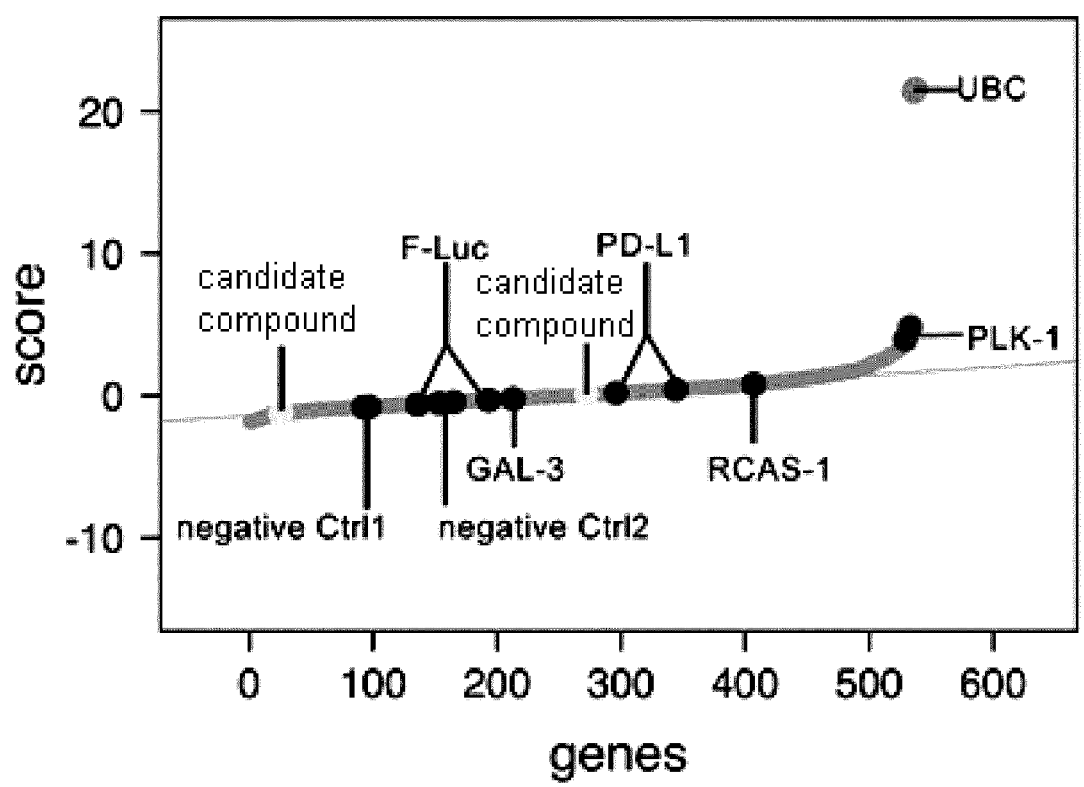

For better candidate visualization and hit analysis, we ranked genes based on a differential score between their toxicity and viability values for both screens (FIGS. 2C and 2D). Out of the top 150 hits from each of both screens, 52 genes were found to be overlapping (p <0.001, hypergeometric testing) and 10 of them were excluded on the basis of their intrinsic impact on tumor cell viability (FIGS. 2E and 3B). Of the identified remaining 42 compounds, based on their CTL-toxicity score, 21 genes were ranked below RCAS-1, 19 genes were ranked between RCAS-1 and Gal-3 and 2 genes between Gal-3 and PD-L1, but none were found to have a stronger impact on tumor cell lysis than PD-L1—indicating its relative importance in immune modulation of anti-tumor T cell responses. Beside others, several sensory receptors were identified.

Network analysis using the Ingenuity Pathways Analysis tool linked several of the gene hits. However, not much is known about the signaling pathways or their potential involvement in the immune system for sensory receptors such as taste receptors (TAS2R, TAS2R3), olfactory receptors (OR1F1, OR2J2, OR51E2) and photoreceptors (OPN3).

Taken together, the Luc-CTL screening approach reliably identified three already known immune modulatory genes and in addition suggested 42 additional candidates including a number of various sensory receptors with potential immune modulatory function in cancer, particularly breast cancer.

Validation of Immune Modulatory Function of Selected Candidate Genes

In order to explore the validity of the screening and candidate identification process, we next functionally validated the immune modulatory capacity of selected candidate genes identified by the method above. To this end we chose two candidate genes ranked at lower to intermediate positions in our screens, (FIGS. 2C and 2D).

To assess a potential influence of such candidate polypeptide identified by the method above on the activation and cytotoxic potential of tumor-specific CTL we co-cultured CTL clones specific for the breast tumor associated antigens survivin or Her-2/neu (Conrad et al., 2008) with the HLA-matched candidate molecule expressing breast cancer cell lines KS and MCF7—which express both tumor antigens. While CTL recognized these tumor antigens when they were presented by the antigen presenting T2 cell line, CTL reactivity against both tumor cell lines was low as shown by low secretion of IFN-gamma and perforin and by low cytotoxic activity. For a candidate polypeptide identified by the method above, a knockdown or blockade by specific antibodies resulted in a strong and dose-dependent increase of T cell activity and tumor cell lysis. We also detected a strong increase in cytotoxic activity of healthy donor derived CD8+ cytotoxic T cells against MCF7-C6 breast cancer cells after blockade or knockdown which was comparable to that achieved by knockdown of PDL1.

Next, we wondered, whether blockade of expression would also increase the capacity of tumor-specific CTL to control breast tumor growth in vivo. To this end we xenografted KS tumor cells into NOD/Scid mice. When tumors had reached volumes of app. 200 mm$^3$, the mice were treated with blocking antibodies against a candidate polypeptide identified by the method above and with $5\times10^6$ survivin-specific CTL. While blockade or CTL transfer alone did not significantly influence tumor development, their combination abrogated further tumor outgrowth in a dose-dependent manner, indicating that successful immunotherapy against breast cancer cells in this context was inhibited by candidate polypeptide identified by the method above, which could be efficiently reversed upon blockade of the identified polypeptide.

Taken together, our data validate the candidate polypeptide identified by the method above as immune modulatory ligands on cancer cells that confer immune protection from CTL mediated lysis through the inhibition of T cell function. Since blockade by specific mAb efficiently restored anti-tumor T cell activity in vitro and in vivo, and when a candidate polypeptide identified by the method above is expressed on many epithelial cancers, it may represent a promising target for therapeutic immune checkpoint control in cancers, in particular epithelial cancers.

We selected further candidates for functional validation, for which we identified not only polypeptides expressed by the cells as candidate but also their ligands as potential immune modulatory genes in both screens—indicating that this signaling axis might play a role in immune regulation.

Using single siRNAs against a polypeptide identified by the method above from the pool of siRNAs we first evaluated the best-performing siRNA sequences based on their capacity to down-regulate its mRNA and protein levels. The functional effect of the individual siRNAs on T cell mediated cytotoxicity was also evaluated using the Luc-CTL assay, which well correlated with the mRNA and protein knockdown efficiency for individual siRNAs. The siRNA sequence most effective in down-regulating expression, as well as in elevating the T cell induced tumor lysis and was therefore chosen for further functional studies. None of the siRNAs by themselves had a major impact on cell viability, as measured by the CTG assay. Knockdown markedly increased tumor lysis by survivin-specific T cells. With the siRNA pool tumor lysis was comparable to that observed with PD-L1 knockdown, whereas with a single siRNA the effect could be even stronger. Conversely, forced overexpression of a polypeptide identified above in MCF7 cells resulted in reduced tumor cell lysis, demonstrating that high expression thereof could enable immune escape of cancer cells. Knockdown of a polypeptide identified above in MCF7 cells also significantly increased the secretion of IFN-γ and cytolytic enzyme granzyme B by survivin-specific T cells as measured by the ELISpot assay.

Moreover, knockdown of expression resulted in a marked increase in tumor cell lysis by survivin-CTLs in another metastatic breast tumor cell line MDA-MB-231, suggesting that the polypeptide mediated immune-resistance is not restricted to a particular cell line.

Taken together these data suggest that tumor-specific expression of a polypeptide identified by the method above suppresses T-cell mediated tumor recognition and lysis in cancer cells, particularly in breast cancer cells.

To account for the increased anti-tumor CTL response upon tumor-specific knockdown of a candidate polypeptide identified by the method above, we evaluated the cytokine levels in the supernatant from the co-culture of control-siRNA treated or candidate polypeptide minis (siRNA treated) MCF7 cells and survivin-specific T cells. T-helper-1 (Th1) cytokines such as IFN-γ, interleukin-2 (IL-2) and tumor necrosis factor-alpha (TNF-α), as well as IL-17, were found to be significantly elevated in the co-culture supernatant from knockdown cells in comparison to the control knockdown. Moreover, there was a significant decrease in the level of immunosuppressive cytokine IL-10 upon candidate polypeptide knockdown. To assess whether the reduced cytokine levels resulted from candidate polypeptide-mediated impairment of T cell activation, we performed TCR phospho-plex analysis in survivin-specific CTLs after direct, short-term contact with control-siRNA treated and candidate polypeptide minus MCF7 cells. Tumor-specific knockdown had no major impact on activation of the TCR signaling components, indicating that an alternate pathway is involved in mediating candidate polypeptide specific immune suppression. One such alternative route is the STAT (signal transducer and activator of transcription) family of transcription factors since they are known to regulate the expression of various cytokines in T cells Yu et al., 2009). Hence, we performed phospho-plex analysis to determine the activation of STAT proteins in survivin-specific T cells when co-cultured with knockdown and control MCF7 cells. While no appreciable difference was observed in the activation status of STAT2, STAT3 and STAT6, there was a marked increase in STAT1 and STAT5a/b signaling when T cells were co-cultured with knockdown MCF7 cells compared to the control cells, indicating that effector Th1-type immune response is impeded by tumor-specific candidate polypeptide. No appreciable differences in STAT signaling in MCF7 cells alone were noted upon knockdown, indicating that the overall observed effect in STAT signaling was T cell-specific.

In all, our findings suggest a role for tumor-specific candidate polypeptide in mediating immune suppression in cancer, particularly in breast cancer by impeding the Th1-type immune response.

Screening with Sensory Receptors

A screening with siRNAs directed against sensory receptors as candidate polypeptides has been performed by the methods described above.

Figure 4A:
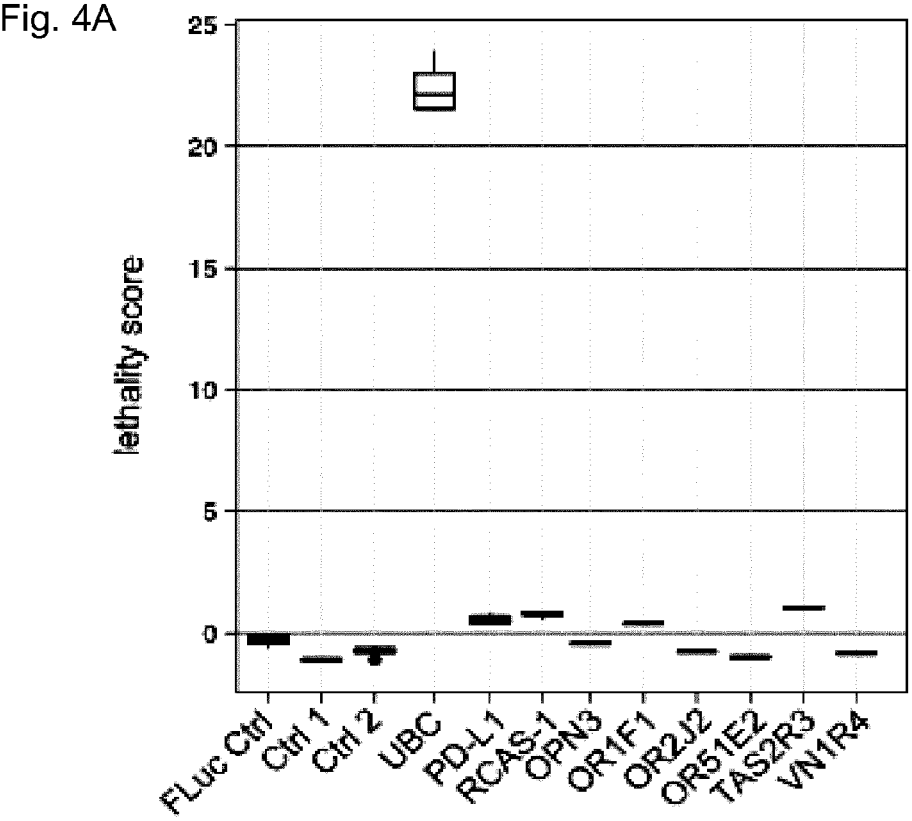
FIG. 4 shows the effect on siRNAs directed against several candidate polypeptides, namely sensory receptors, displayed as the lethality score (A) and as a differential score (B).
Figure 4B:
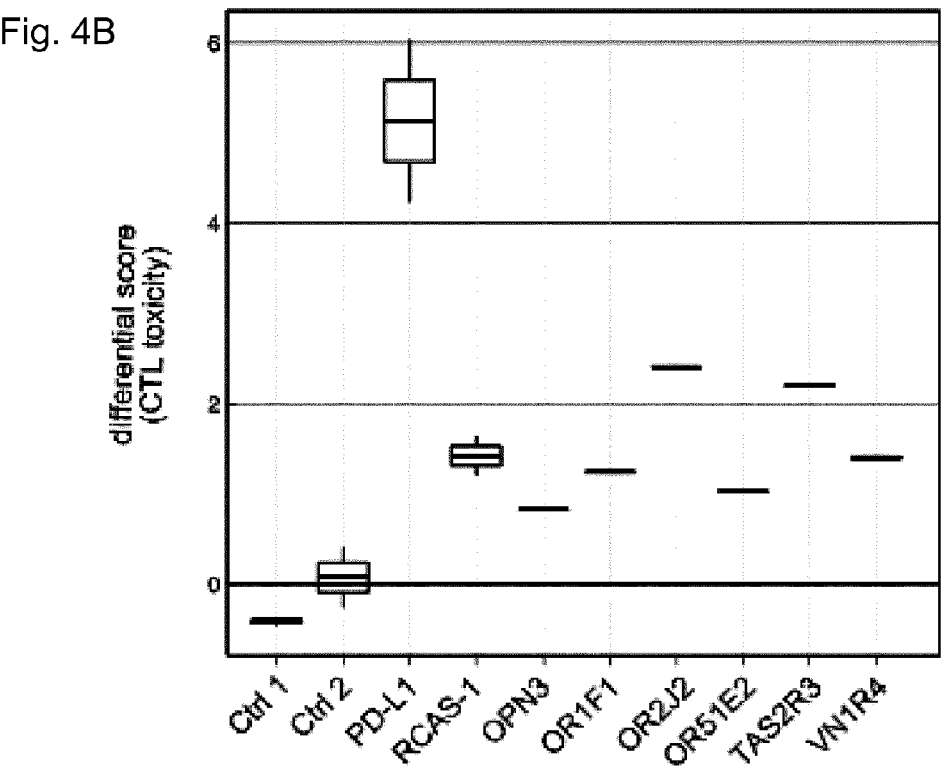

Thereby, results were depicted as a lethality score (FIG. 4A) and a differential score of the CTL toxicity (FIG. 4B). These results clearly show that sensory receptors represent potent targets for modifying CTL response. In particular an olfactory receptor of the family 2 (OR2J2) and a TAS2 receptor (TAS2R3) showed particularly positive results.

The used siRNA mediates the CTL response, namely suppresses it. Therefore, the employed siRNA serves as a compound for mediating the CTL response according to the present invention.

Discussion

Here we report a high-throughput screening strategy to comprehensively identify new cancer-associated immune-checkpoint molecules that promote immune-resistance in tumors.

By means of said method, we have identified a number of sensory receptors as a therapeutic and diagnostic target that can be used in in vivo and in vitro therapy and diagnosis.

In our hands the chosen luciferase-based determination of tumor cell death correlated well with classical cytotoxicity tests and was suitable for application in a high-throughput format. Since the use of fresh primary CD8+ T cells from different healthy donors imposes variability, we performed the entire screen twice, each time in duplicates. Thereby we were able to obtain reproducible and overlapping candidates. By reliably confirming 3 already established immune modulatory ligands in breast cancer cells, the screening procedure proved its capacity to identify immune modulatory ligands on tumor cells. Among the 520 tested genes in total, 42 new candidates with potential impact on tumor lysis capacity of CTL were identified. Compared to whole genome-based screens this yield of approximately 8% appears high and warrants careful functional validation of the identified targets. However, immune response-related genes represent a major proportion of the genome and our screening library, which included only cell surface-associated molecules, was enriched in cell surface signaling proteins that might play a role in immune modulation (Zhu et al., 2011). Moreover, a previous screen on NK cell modulating ligands reported by Bellucci et al. also revealed a high number of NK modulating genes (Bellucci et al., 2012). Our high discovery rate might thus indeed represent complex genetic networks governing suppression of immune surveillance in cancer patients. So far, we have performed experimental validation of several identified candidates using additional tumor cell lines and tumor antigen-specific CTL clones and in all cases we could confirm their immune modulatory function.

Interestingly, the identified candidates also included sensory receptors and peptides—imposing new targets for diagnostic or therapeutic exploitation.

Taken together, we here introduce an effective design of a high-throughput screen to uncover a broad panel of new immune-suppressor genes in cancer. This screen could also be used to identify genes that, when expressed in other cells showing a pathologic CTL response, confer susceptibility towards immune attack. Identification of both these subset of genes may be exploited as potential biomarkers for better patient stratification and for evaluating clinical response to cancer immunotherapy. In addition, slight modifications of the screening approach presented herein could allow for the identification of chemical or biological compounds that enhance CTL-mediated cell killing. In all, our methodology may enable the characterization of the entire "immune modulatome" of cells having a pathological CTL response which might serve as a basis for the selection of promising target molecules for the development of therapeutic strategies involving blocking antibodies or chemical compounds.

Further, we identified sensory receptors as molecular target structures for modulating CTL response and ligands thereof as therapeutic and diagnostic compounds for use in methods for treating, preventing or diagnosing a pathologic CTL response.

Example 2

Additional experiments were conducted to support the initial finding that TAS2R3 and OR51E2 are immune modulatory ligands on tumor cells, that their inhibition would increase anti-tumor activity of tumor-specific T cells and that therefore these are promising targets for anticancer immunotherapy. The experiments are summarized below as follows:

TAS2R3

Figure 5A:
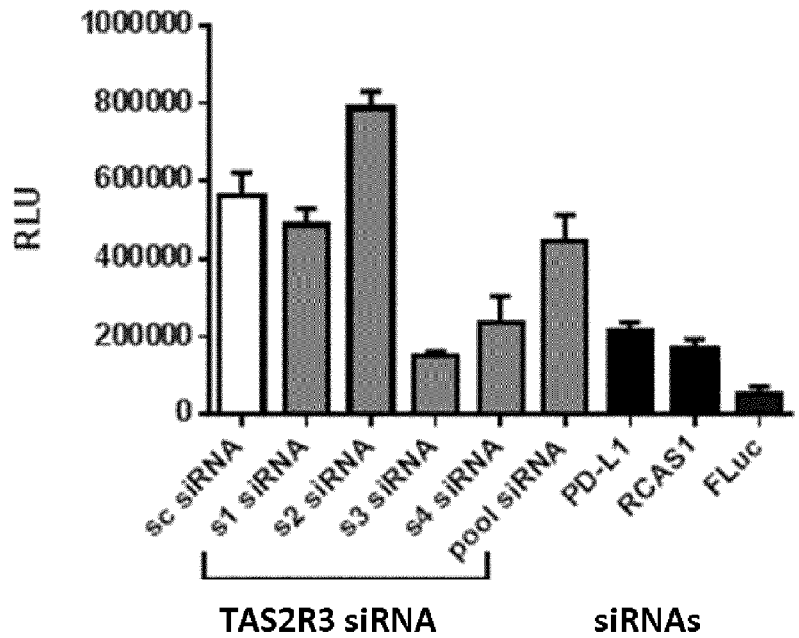
FIG. 5 shows the viability of luciferase transfected MCF7 breast tumor cells transfected with different gene specific siRNAs as measured by luciferase activity (RLU) after co-culture with tumor antigen specific cytotoxic T cells (survivin specific CTL clone) (A) or without T cell co-culture (B). Reduced luciferase activity indicates tumor cell death. Unspecific scrambled siRNA (sc RNA) was used as negative control; luciferase specific siRNA (fluc) as positive control.
Figure 5B:
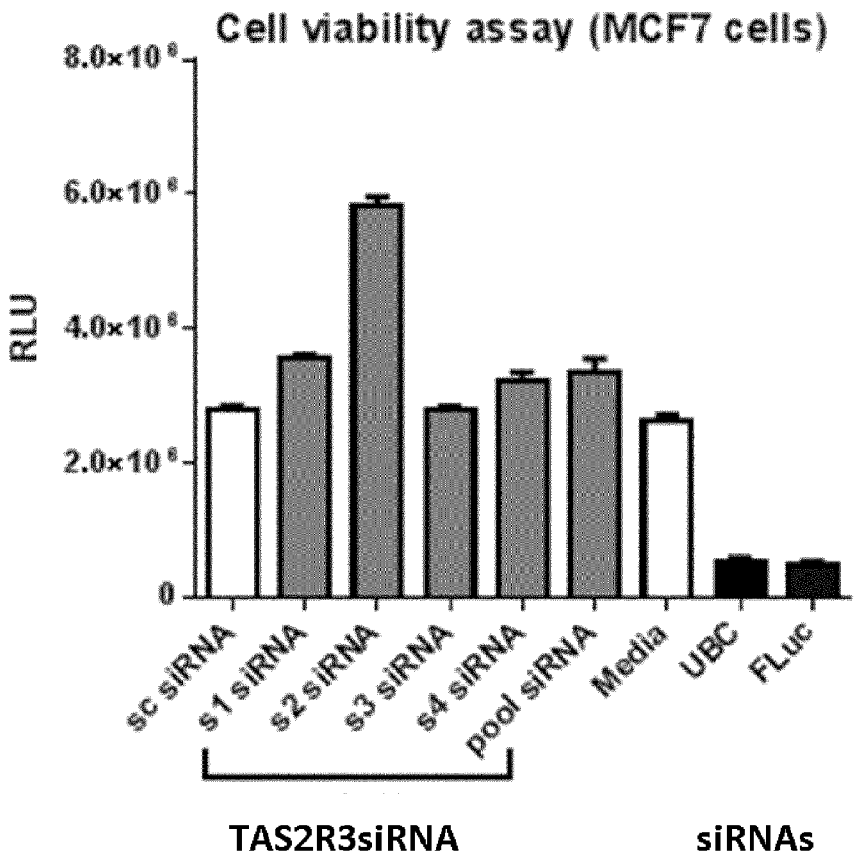

The TAS2R3 siRNA pool used for the HTP screen was deconvoluted, demonstrating that siRNAs s3 and s4 significantly increase T cell mediated lysis of luciferase transfected MCF7 breast cancer target cells as indicated by significant reduction of luciferase activity which was comparable to that achieved by knockdown of a well established and clinically relevant immune checkpoint molecules, PDL1 and RCAS1 (FIG. 5A). In contrast, these siRNAs had no impact on viability of luciferase transfected MCF7 breast cancer cells in the absence of T cells (FIG. 5B), while knockdown of ubiquitin (ubc) which is essential for cell viability strongly decreased cell survival and was used as an internal positive control for the assay system. As an additional internal control, knock down of luciferase (fluc) in MCF7 cells was used.

Figure 6:
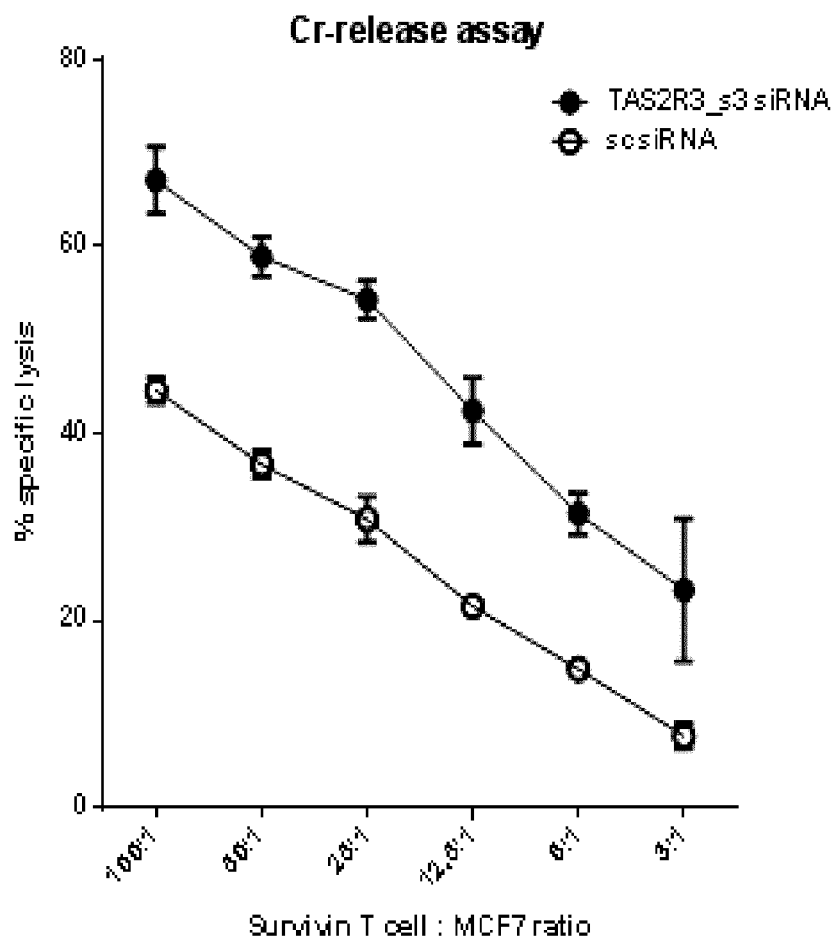
FIG. 6 shows a chromium-release assay to assess the T cell mediated extent of tumor cell lysis in MCF7 breast cancer cells after TAS2R3 gene knock down. Transfection with unspecific scrambled siRNA (sc RNA) served as negative control.

It was further shown that TAS2R3 knock down in MCF7 tumor cells significantly increases their lysis by tumor-specific T cells in a classical cytolysis experiment (Chromium release assay; FIG. 6).

Figure 7:
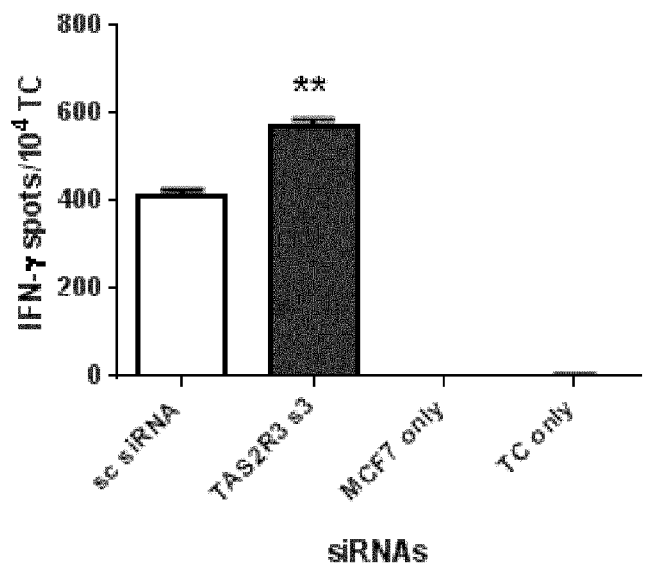
FIG. 7 shows an IFN-gamma Elispot assay to assess the numbers of survivin specific T cells reacting to encounter with TAS2R3-proficient (sc siRNA) or -deficient (TAS2R3 siRNA) by IFN-gamma secretion. Transfection with unspecific scrambled siRNA (sc RNA) served as negative control.
Figure 8:
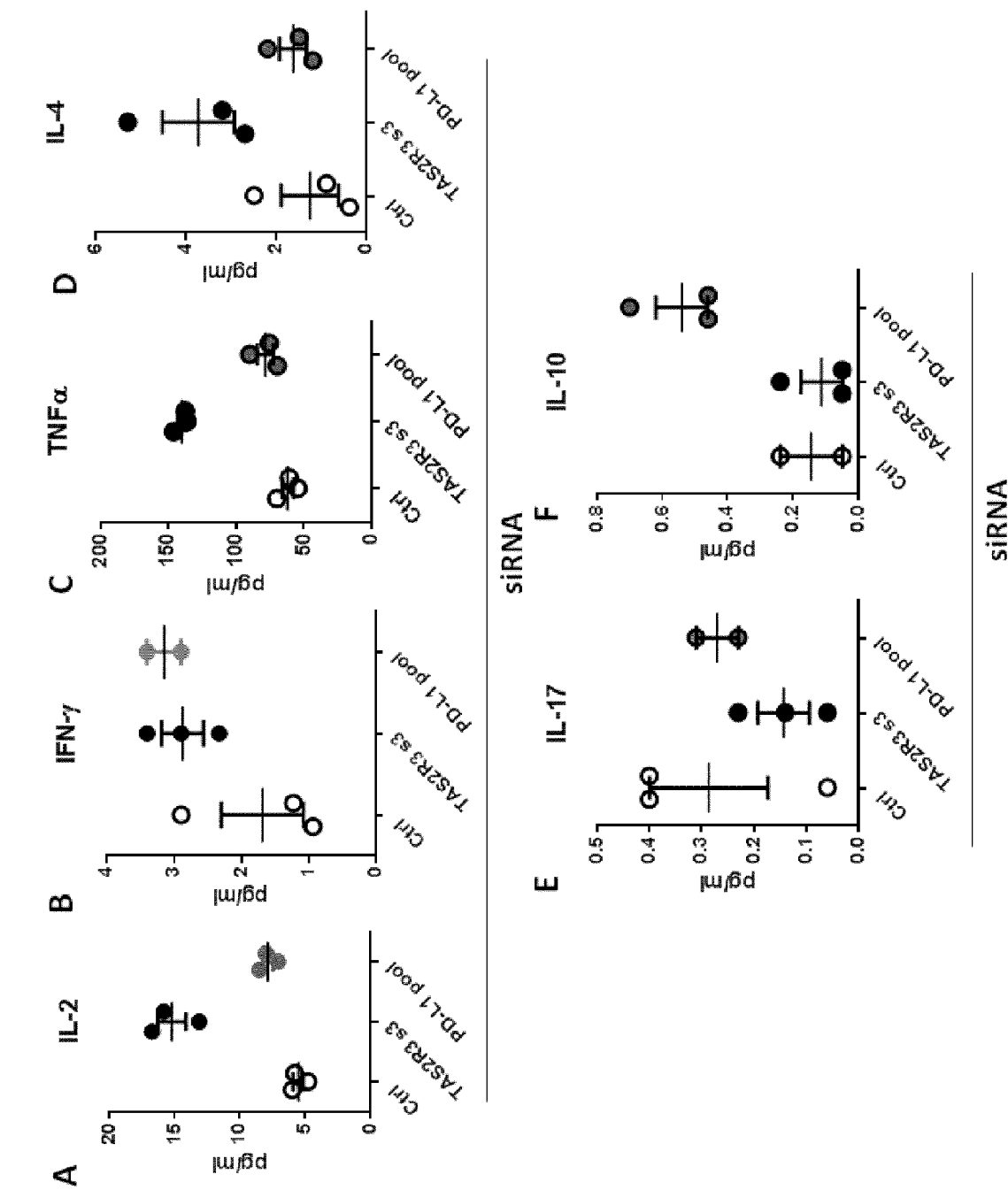
FIG. 8 shows the cytokine contents in supernatants of survivin specific T cells co-cultured with survivin expressing MCF7 breast cancer cells that were either TAS2R3-proficient (ctrl) or -deficient (TAS2R3 siRNA_s3) in comparison to PDL-1 deficient (PDL1 siRNA pool) as detected by Luminex analysis. Each dot represents one replicate of the experiment.

We then showed that TAS2R3 knockdown in MCF7 breast tumor cells increased the functional activity of co-cultured tumor specific T cells in regard to: i) increased numbers of activated T cells (indicated by increased numbers of IFN-gamma secreting T cells in IFN-gamma Elispot assay) (FIG. 7); and ii) increased amounts of T cell effector cytokines IFN-gamma, TNF-alpha, IL-2, IL-4 (FIG. 8A-D) released by T cells into the co-culture supernatant, while the release of immune suppressive cytokines IL-10 and IL-17 was unaffected (FIGS. 8E and 8F).

Figure 9:
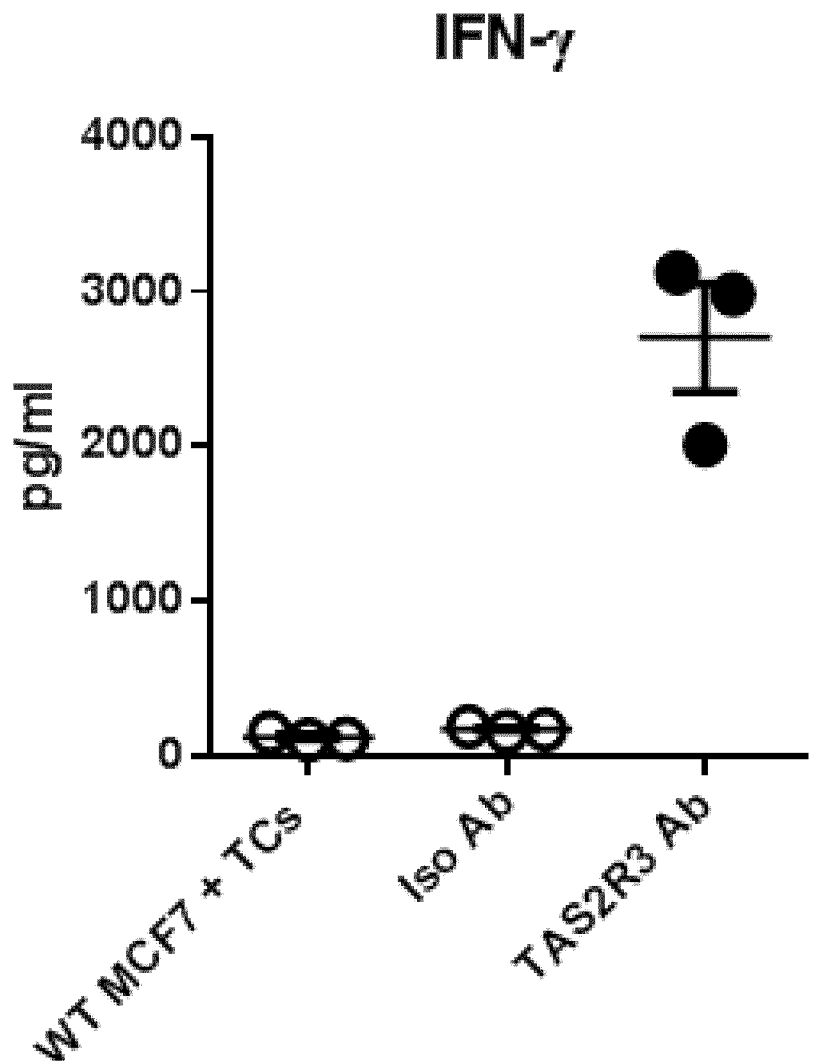
FIG. 9 shows the IFN-gamma content in supernatants of survivin specific T cells co-cultured with survivin expressing MCF7 breast cancer cells either TAS2R3-proficient (wt MCF7, iso Ab) or -deficient (TAS2R3Ab) as detected by Luminex analysis. Each dot represents one replicate of the experiment. TAS2R3 inhibition was conducted by specific antibodies (anti-TAS2R3 antibody ab65488; abcam) in comparison to a respective isotype control.

Finally, we demonstrate that increased expression of IFN-gamma can also be achieved by blocking of TAS2R3 on the surface of breast tumor cells by TAS2R3 specific antibody (FIG. 9).

OR51E2

Figures 10A, 10B:
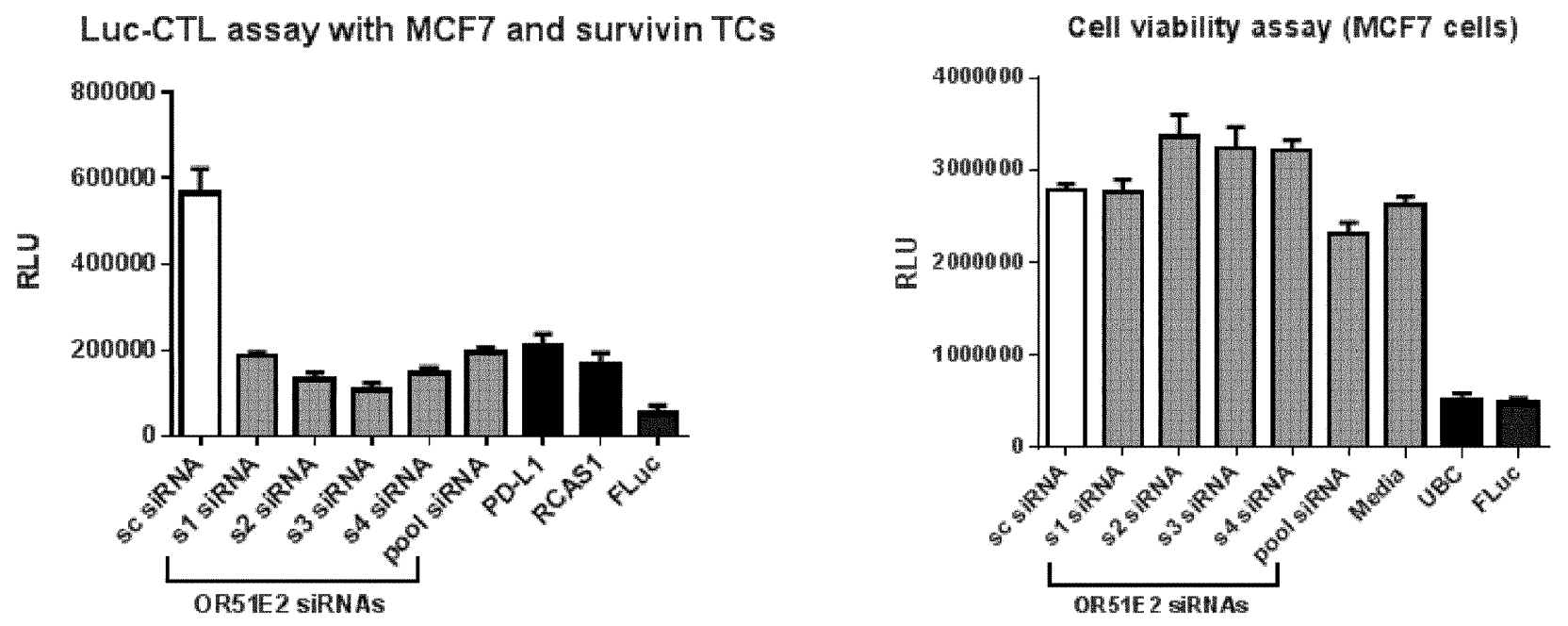

In analogy to validation experiments with TAS2R3 we deconvoluted the OR51E2 siRNA pool used for the HTP screen, demonstrating that all siRNAs in the pool significantly increased T cell mediated lysis of luciferase transfected MCF7 breast cancer target cells as indicated by significant reduction of luciferase activity which was comparable to that achieved by knockdown of a well established and clinically relevant immune checkpoint molecules, PDL-1 and RCAS1 (FIG. 10A). In contrast, these siRNAs had no impact on viability of luciferase transfected MCF7 breast cancer cells in the absence of T cells (FIG. 10B), while knockdown of ubiquitin (ubc) which is essential for cell viability strongly decreased cell survival and was used as an internal positive control for the assay system. As an additional control, knock down of luciferase (fluc) in MCF7 cells was used.

Figure 11:
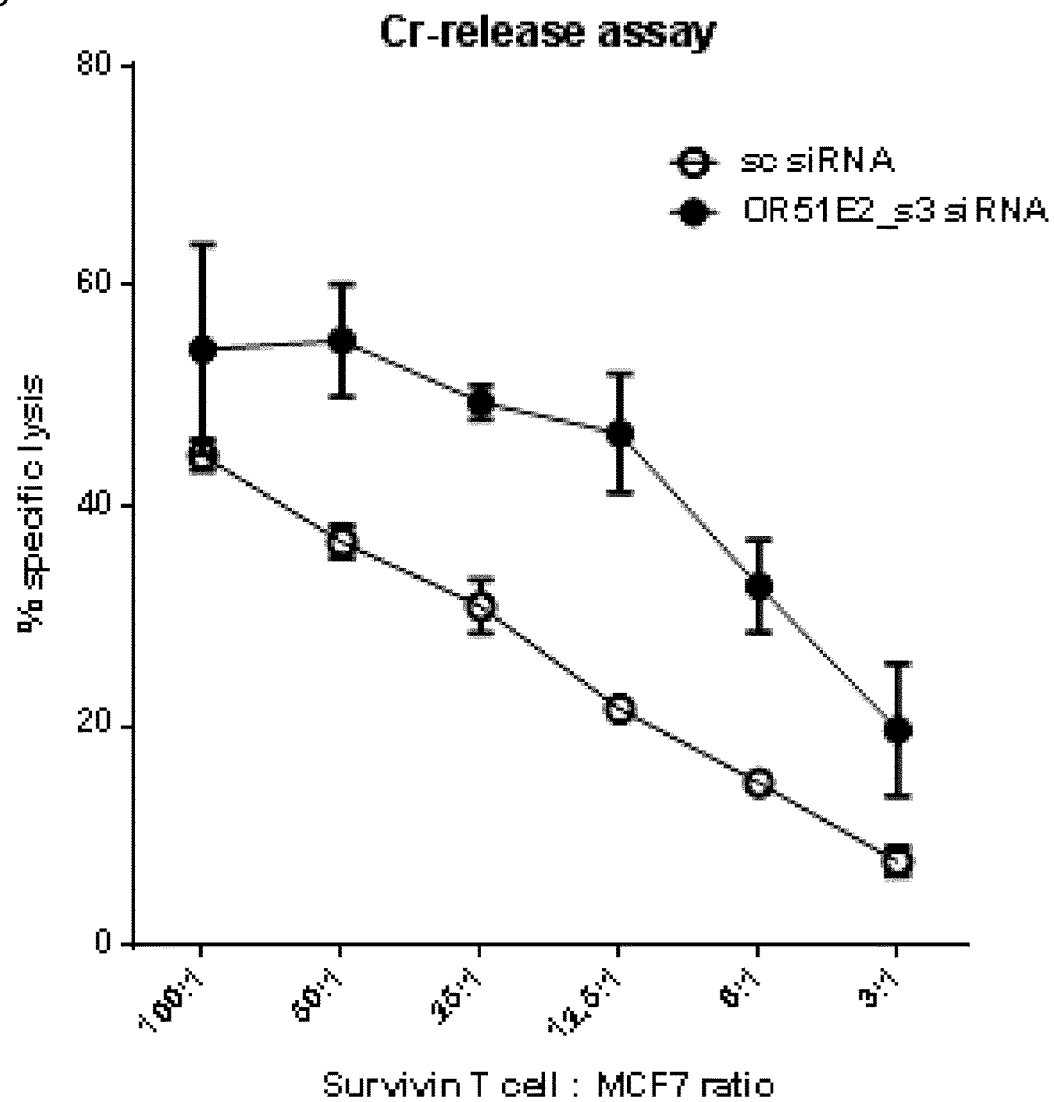
FIG. 11 shows a chromium-release assay to assess the T cell mediated extent of tumor cell lysis in MCF7 breast cancer cells after OR51E2 gene knock down. Transfection with unspecific scrambled siRNA (sc RNA) served as negative control.

We further show that OR51E2 knock down in MCF7 tumor cells significantly increases their lysis by tumor specific T cells in a classical cytolysis experiment (Chromium-release assay; FIG. 11).

Taken together, further evidence is provided for the immune suppressive role of TAS2R3 and OR15E2 which can be blocked by gene knockdown or by antibody blockade.

REFERENCES

1. Rabinovich, G. A., D. Gabrilovich, and E. M. Sotomayor, Immunosuppressive strategies that are mediated by tumor cells. Annu Rev Immunol, 2007. 25: p. 267-96.
2. Zitvogel, L., A. Tesniere, and G. Kroemer, Cancer despite immunosurveillance: immunoselection and immunosubversion. Nat Rev Immunol, 2006. 6(10): p. 715-27.
3. Pardoll, D. M., The blockade of immune checkpoints in cancer immunotherapy. Nat Rev Cancer, 2012. 12(4): p. 252-64.
4. Blank, C., et al., PD-L1/B7H-1 inhibits the effector phase of tumor rejection by T cell receptor (TCR) transgenic CD8+ T cells. Cancer Res, 2004. 64(3): p. 1140-5.
5. Chambers, C. A., et al., CTLA-4-mediated inhibition in regulation of T cell responses: mechanisms and manipulation in tumor immunotherapy. Annu Rev Immunol, 2001. 19: p. 565-94.
6. Brahmer, J. R., et al., Safety and activity of anti-PD-L1 antibody in patients with advanced cancer. N Engl J Med, 2012. 366(26): p. 2455-65.
7. Topalian, S. L., et al., Safety, activity, and immune correlates of anti-PD-1 antibody in cancer. N Engl J Med, 2012. 366(26): p. 2443-54.
8. van Elsas, A., A. A. Hurwitz, and J. P. Allison, Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med, 1999. 190(3): p. 355-66.
9. FDA approves new treatment for a type of late-stage skin cancer [press release]. Mar. 25, 2011.
10. Weber, J., Review: anti-CTLA-4 antibody ipilimumab: case studies of clinical response and immune-related adverse events. Oncologist, 2007. 12(7): p. 864-72.
11. Berrien-Elliott, M. M., et al., Durable Adoptive Immunotherapy for Leukemia Produced by Manipulation of Multiple Regulatory Pathways of CD8+ T-Cell Tolerance. Cancer Res, 2013. 73(2): p. 605-16.
12. Woo, S. R., et al., Immune inhibitory molecules LAG-3 and PD-1 synergistically regulate T-cell function to promote tumoral immune escape. Cancer Res, 2012. 72(4): p. 917-27.
13. Bellucci, R., et al., Tyrosine kinase pathways modulate tumor susceptibility to natural killer cells. J Clin Invest, 2012. 122(7): p. 2369-83.
14. Hill, H. R. and T. B. Martins, The flow cytometric analysis of cytokines using multi-analyte fluorescence microarray technology. Methods, 2006. 38(4): p. 312-6.
15. Bachmann, M. F., et al., Distinct kinetics of cytokine production and cytolysis in effector and memory T cells after viral infection. Eur J Immunol, 1999. 29(1): p. 291-9.
16. Slifka, M. K., F. Rodriguez, and J. L. Whitton, Rapid on/off cycling of cytokine production by virus-specific CD8+ T cells. Nature, 1999. 401(6748): p. 76-9.
17. Strauss, G., et al., Without prior stimulation, tumor-associated lymphocytes from malignant effusions lyse autologous tumor cells in the presence of bispecific antibody HEA125xOKT3. Clin Cancer Res, 1999. 5(1): p. 171-80.
18. Dong, H., et al., Tumor-associated B7-H1 promotes T-cell apoptosis: a potential mechanism of immune evasion. Nat Med, 2002. 8(8): p. 793-800.
19. Brunner, K. T., et al., Quantitative assay of the lytic action of immune lymphoid cells on 51-Cr-labelled allogeneic target cells in vitro; inhibition by isoantibody and by drugs. Immunology, 1968. 14(2): p. 181-96.
20. Han, Y., W. Qin, and G. Huang, Knockdown of RCAS1 expression by RNA interference recovers T cell growth and proliferation. Cancer Lett, 2007. 257(2): p. 182-90.
21. Peng, W., et al., Tumor-associated galectin-3 modulates the function of tumor-reactive T cells. Cancer Res, 2008. 68(17): p. 7228-36.
22. Conrad, H., et al., CTLs directed against HER2 specifically cross-react with HER3 and HER4. J Immunol, 2008. 180(12): p. 8135-45.
23. Brackertz, B., et al., FLT3-regulated antigens as targets for leukemia-reactive cytotoxic T lymphocytes. Blood Cancer J, 2011. 1(3): p. e11.
24. Yu, H., D. Pardoll, and R. Jove, STATs in cancer inflammation and immunity: a leading role for STAT3. Nat Rev Cancer, 2009. 9(11): p. 798-809.
25. Gao, J., et al., Advances in the development of cancer immunotherapies. Trends Immunol, 2013. 34(2): p. 90-8.
26. Zhu, Y., S. Yao, and L. Chen, Cell surface signaling molecules in the control of immune responses: a tide model. Immunity, 2011. 34(4): p. 466-78.
27. Gilbert, D. F., et al., A novel multiplex cell viability assay for high-throughput RNAi screening. PLoS One, 2011. 6(12): p. e28338.
28. Brown, C. E., et al., Biophotonic cytotoxicity assay for high-throughput screening of cytolytic killing. J Immunol Methods, 2005. 297(1-2): p. 39-52.
29. Muller, P., et al., Identification of JAK/STAT signalling components by genome-wide RNA interference. Nature, 2005. 436(7052): p. 871-5.
30. Boutros, M., L. P. Bras, and W. Huber, Analysis of cell-based RNAi screens. Genome Biol, 2006. 7(7): p. R66.

The invention claimed is:

1. A method for identifying an agent influencing the response of cells to CTLs, said method comprising the steps:
   (i) providing cells expressing at least one surface polypeptide preventing CTL response, and further also expressing a polypeptide enabling bioluminescence,
   (ii) contacting cells of step (i) with at least one agent of interest,
   (iii) co-incubating cells obtained from step (ii) with CTLs and an agent crosslinking the antigen receptors of the CTLs with a cell-surface molecule of the cells of step (ii),
   (iv) recovering the viable cells obtained from step (iii),
   (v) determining the bioluminescence of the cytosol of the cells obtained from step (iv), and
   (vi) comparing the bioluminescence of the cells contacted with at least one agent and with a negative control of cells not contacted with an agent and/or with one or more other agent(s).

2. The method according to claim 1, wherein the CTLs are pre-activated CD8+ T-cells, CD8+ T cells pre-activated by T cell receptor (TCR) stimulation through a CD3 specific antibody and/or a CD28 specific antibody.

3. The method according to claim 1, wherein the agent is an interfering RNA.

4. The method according to claim 3, wherein the agent is siRNA targeting mRNA encoding for the expression activity of a polypeptide typically localized at the cell surface and/or involved in cell signaling.

5. The method according to claim 3 as a high-throughput RNAi screen for: (i) detection of immune-checkpoint molecules that mediate tumor resistance to CTLs; or (ii) determination of immune-modulatory genes in tumors.

6. The method according to claim 1, wherein the agent is or comprises one or more amino acid moieties; and/or a polypeptide strand.

7. The method according claim 1 wherein a library of different agents is tested.

8. The method according claim 1, wherein the surface polypeptide is a sensory receptor that functions as an immune-checkpoint molecule.

9. The method according to claim 8, wherein the sensory receptor is selected from the group consisting of
   (a) an olfactory receptor, and
   (b) an opsin.

10. The method according claim 1, wherein said cells are transfected in order to obtain larger amounts of the at least one surface polypeptide.

11. The method according claim 1, wherein the crosslinking agent is a crosslinking antibody.

12. The method according claim 11, wherein the crosslinking antibody has at least two binding species: one against a T cell surface receptor, the other to a polypeptide present on the cell.

13. The method according to claim 1, wherein said cells are mammalian cells.

14. The method according claim 13, wherein said cells are of human origin.

15. The method according claim 13, wherein said cells are cells involved in abnormal growth.

16. The method according to claim 1, wherein the surface polypeptide is a sensory receptor.

17. The method according to claim 1, wherein the polypeptide enabling bioluminescence is luciferase.

18. The method according to claim 3, wherein the interfering RNA is complementary to messenger ribonucleic acid (mRNA) encoding for a polypeptide typically localized at the cell surface and/or involved in cell signaling.

19. The method according to claim 3, wherein the interfering RNA is small interfering ribonucleic acid (siRNA) or small hairpin RNA (shRNA).

20. The method according to claim 6, wherein the agent is or comprises a peptide or protein.

21. The method according to claim 6, wherein the agent is or comprises an antibody or a fragment thereof.

22. The method according to claim 1, wherein the agent is or comprises a molecule comprising a molecular weight of between 500 Da and 100 kDa.

23. The method according to claim 1, wherein, the agent is or comprises a molecule having a molecular weight of not more than 500 Da.

24. The method according to claim 16, wherein the sensory receptor is an olfactory receptor.

25. The method according to claim 16, wherein the sensory receptor is a taste receptor, a pheromone receptor or a vomeronasal receptor.

26. The method according to claim 25, wherein the sensory receptor is a taste receptor type 2 (TAS2R) or a vomeronasal 1 receptor.

27. The method according to claim 24, wherein the olfactory receptor is an olfactory receptor of family 1, 2 or 51.

28. The method according to claim 24, wherein the olfactory receptor is an olfactory receptor of family 1 subfamily F (OR1F), family 2 subfamily J (OR2J) or family 51 subfamily E (OR51E).

29. The method according to claim 16, wherein the sensory receptor is taste receptor type 2 member 3 (TAS2R3).

30. The method according to claim 24, wherein the olfactory receptor is olfactory receptor of family 1 subfamily F member 1 (OR1F1).

31. The method according to claim 24, wherein the olfactory receptor is olfactory receptor of family 2 subfamily J member 2 (OR2J2).

32. The method according to claim 24, wherein the olfactory receptor is olfactory receptor of family 51 subfamily E member 2 (OR51E2).

33. The method according to claim 25, wherein the sensory receptor is vomeronasal 1 receptor 4 (VN1R4).

34. The method according to claim 16, wherein the sensory receptor is opsin 3 (OPN3).

35. The method according to claim 10, wherein the cell does not naturally express the at least one surface polypeptide and is transfected with an active gene encoding the at least one surface polypeptide.

36. The method according to claim 15, wherein the cells are neoplastic cells or cancer cells.

37. The method according to claim 14, wherein the cells are obtained from a patient directly, or are progeny of such cells.

38. The method according to claim 12, wherein the T cell surface receptor is CD3 and/or the polypeptide present on the cell is EpCAM.

39. The method according to claim 1, wherein the viable cells are recovered by: (i) washing away unviable cells from adherent viable cells; or (ii) FACS.

40. The method according to claim 1, wherein the bioluminescence is determined by lysing or sonicating the viable cells.

41. The method according to claim 1, wherein the bioluminescence is determined by addition of an appropriate bioluminescence precursor compound and respective cofactors and by detection of the bioluminescence.

42. The method according to claim 1, wherein a difference in bioluminescence between the cells contacted with at least one agent and with a negative control of cells not contacted with an agent and/or with one or more other agent(s) corresponds reciprocally to a difference in CTL response between the cells compared.

43. The method according to claim 1, wherein a decrease in bioluminescence in cells contacted with at least one agent compared to a negative control of cells not contacted with an agent and/or with one or more other agent(s) identifies an agent that increases CTL response compared to the negative control or the one or more other agent(s).

* * * * *